(12) United States Patent
Stloukal

(10) Patent No.: US 8,241,890 B2
(45) Date of Patent: Aug. 14, 2012

(54) INDUSTRIAL PRODUCTION DEVICE COMPRISING CONTINUOUS CONVEYOR BELT FOR PRODUCING IMMOBILIZED BIOCATALYSTS

(75) Inventor: Radek Stloukal, Ceska Lipa (CZ)

(73) Assignee: Lentikat's, A.S., Praha (CZ)

( * ) Notice: Subject to any disclaimer, the term of this patent is extended or adjusted under 35 U.S.C. 154(b) by 813 days.

(21) Appl. No.: 12/281,661

(22) PCT Filed: Mar. 6, 2007

(86) PCT No.: PCT/CZ2007/000015
§ 371 (c)(1),
(2), (4) Date: Sep. 12, 2008

(87) PCT Pub. No.: WO2007/104268
PCT Pub. Date: Sep. 20, 2007

(65) Prior Publication Data
US 2009/0061499 A1 Mar. 5, 2009

(30) Foreign Application Priority Data

Mar. 13, 2006 (CZ) ................................. 2006-17510
Mar. 13, 2006 (CZ) ................................. 2006-17511

(51) Int. Cl.
| C12M 1/00 | (2006.01) |
| C12P 1/00 | (2006.01) |
| C12P 19/02 | (2006.01) |
| C12P 7/56 | (2006.01) |
| C12P 7/06 | (2006.01) |
| C12N 11/02 | (2006.01) |
| C12N 11/08 | (2006.01) |
| C12N 11/04 | (2006.01) |
| A62D 3/02 | (2007.01) |

(52) U.S. Cl. ....... 435/283.1; 435/41; 435/105; 435/139; 435/161; 435/177; 435/180; 435/182; 435/262.5

(58) Field of Classification Search .................. None
See application file for complete search history.

(56) References Cited

U.S. PATENT DOCUMENTS

| 5,137,031 A * | 8/1992 | Guirguis | 600/584 |
| 5,229,487 A * | 7/1993 | Tsubakimoto et al. | 528/484 |
| 5,236,412 A * | 8/1993 | Lloyd et al. | 604/20 |
| 5,283,123 A * | 2/1994 | Carter et al. | 428/403 |
| 5,629,187 A * | 5/1997 | Ors et al. | 435/178 |
| 5,977,014 A * | 11/1999 | Plischke et al. | 502/401 |
| 6,994,209 B2 * | 2/2006 | Cediel et al. | 198/847 |
| 2003/0017959 A1 * | 1/2003 | Baeck et al. | 510/445 |

FOREIGN PATENT DOCUMENTS

WO    WO 99/67320    12/1999

OTHER PUBLICATIONS

Rebros M et al: "High efficiency ethanol fermentation by entrapment of Zymomonas mobilis into LentiKats ((R))" Letters in Applied Microbiology, vol. 41, No. 5, 2005, pp. 412-416.
Rosenberg M et al: "High Temperature Lactic Acid Production by *Bacillus coagulans* Immobilized i n LentiKats" Biotechnology Letters, Kluwer Academic Publishers, DO, vol. 27, No. 23-24, Dec. 1, 2005, pp. 1943-1947.
Rebros M et al: "A simple entrapment of glucoamylase into Lent iKats<(>R) as an efficient catalyst for maltodextrin hydrolysis"Enzyme and Microbial Technology, Stoneham, MA, US, vol. 39, No. 4, Jan. 26, 2006, pp. 800-804.
Rebros M et al: "Hydrolysis of sucrose by invertase entrapped i n polyvinyl alcohol hydrogel capsules" Food Chemistry, Elsevier Science Publishers Ltd, GB, vol. 102, No. 3, Jan. 19, 2007, pp. 784-787.
Vorlop K-D et al: "Immobilisierte Biokatalysatoren" Nachwachsende Rohstoffe, Landwirtschaftsverlag GMBH, Munster, DE, [Online] vol. 10, 1997, pp. 32-46.
Jahnz U et al: "New matrices and bioencapsulation processes" Focus on Biotechnology: Engineering and Manufacturing for Biotechnology, vol. 4, 2001, pp. 293-307.
International Search Report from PCT/CZ2007/000015 mailed Jul. 26, 2007.

\* cited by examiner

*Primary Examiner* — David Naff
(74) *Attorney, Agent, or Firm* — Oppedahl Patent Law Firm LLC

(57) ABSTRACT

A method and device are disclosed for industrial production of immobilized biocatalysts such as enzymes or microorganisms. In the method, a polyvinyl alcohol gel is produced containing the biocatalysts, and the gel is shaped in a stream of drying air. The device includes a continuous conveyor belt. A casting mechanism is positioned above the belt for applying a mixture containing a biocatalyst to the belt. Positioned for the belt to pass through following the casting mechanism, is a drying channel, a reswelling tank, a wiping and collecting device, a rinse box, and a drying channel.

2 Claims, 4 Drawing Sheets

INDUSTRIAL PRODUCTION DEVICE COMPRISING CONTINUOUS CONVEYOR BELT FOR PRODUCING IMMOBILIZED BIOCATALYSTS

FIELD OF THE INVENTION

The present invention relates to the method for industrial production of biocatalysts with bioactive material in the form of immobilized enzymes, or microorganisms immobilized in polyvinyl alcohol gel, and their use, and also to an industrial production device, which enables optimization of the volume and area of a biological carrier according to the extent of biologically active material, which includes a casting mechanism situated in front of a drying channel, through which a continuous conveyor belt runs.

BACKGROUND OF THE INVENTION

The encapsulation of micro bacteria using a polyvinyl alcohol carrier or a polyurethane carrier is known in the field. The method for the production of a biocatalyst with biologically active material in the form of microorganisms, enzymes, spores and/or cells, which are placed in polyvinyl alcohol gel (referred to as "PVA-gel" in the further text) is disclosed in CZ patent 249 179. PVA-gel as a gel carrier for biologically active material is highly suitable for the production of chemical or biological catalysts. The gel body manufactured according to this method proves higher mechanical stability compared to gel bodies formerly known, particularly in terms of abrasion resistance and tensile strength. Owing to the above mentioned improved mechanical properties, the production of a gel body in a reactive and kinetically suitable lens-shaped form is possible. So the gel body produced is firm and abrasion resistant for more than several months, even at high revolution stirring, compared to those formerly known. Due to the lenticular shape characterized by a large diameter and low height, physically, chemically or biologically active material is always situated closely beneath the surface, which provides its reactive and kinetically useful arrangement. The biotechnological procedures, which utilize PVA-gel as a carrier of biologically active material, are known in the field.

The utilizations of the above mentioned carriers in the process of removing of nitrogen from waste waters are known. Such utilizations are described, for example, in EP0758680 (porous cellulose derivatives), WO09508513 (polyvinyl alcohol, vermiculite, polyurethane) and CN1076488 (polyvinyl alcohol). The mentioned carriers are used (usually) in the immobilization of activated sludge, which is often previously enriched in various ways, in particular by nitrifying bacteria (see, for example, the processes PEGASUS or PEGAZUR), but also directly in the immobilization of pure nitrifying or denitrifying bacteria. As referred to in literature, a very important characteristic of a carrier is the extent of its specific surface with regard to the volume of a reactor, or more precisely to the volume of currently-processed waste waters. That is to say, this parameter is directly related to the size of a reactor and to the waste water holding time in the reactor, because it can be influenced in particular by the amount (or more precisely, by weight or volume) of a carrier with the given specific surface which is placed into a reactor. For example, the nitrogen pollution removal process by means of bacterium immobilized in a polyethylene glycol (PEG) carrier in the shape of tablets with geometrical dimensions S/V=3 and 2, makes it possible to achieve the nitrogen removal rate from 0.34 kg/m$^3$ to 1.14 kg/m$^3$ per day with the content of 2% w/v wet biomass of activated sludge in a carrier. (T. Sumino, H. Nakamura, N. Mori, Y. Kawaguchi: Immobilization of Nitrifying Bacteria by Polyethylene Glycol Prepolymer, Journal of Fermentation and Bioengineering, 73(1), 37-42, 1992.)

However, the extent of the specific (geometric) surface of a carrier with regard to its volume, or more precisely, to its shape and measurements, is coessential parameter, particularly on account of economic reasons. The carriers, shape of which approximates either a ball or cylinder, where the bottom diameter (d) and the height (h) are of an approximately the same value, are still used for removing nitrogen from sewerage water by immobilized cells. The minimal value of the carrier measurement for removing nitrogen from waste waters is 1 mm. The carriers usually used measure 3 mm, which means that the ratio of the surface to the volume of the carrier (S/V) assumes values of approximately 2 mm$^{-1}$ to 6 mm$^{-1}$. If a lens-shaped or band-shaped carrier is used, less of a biocatalyst can be used compared to the current processes using the immobilized cells for nitrogen compounds removal from potable, industrial and waste waters, even at the same or higher intensity of the process.

Another alternative use of a gel carrier in biotechnology processes is in the method for lactic acid production. This acid is widely used, particularly in the food, pharmaceutical and chemical industry, amongst others. Lactic acid is produced by a large number of microorganisms, but primarily by filamentous fungi and bacteria. Of the filamentous fungi, *Rhizopsus arrhizuz*, or *oryzae* is a good lactic acid producer. The indisputable advantage of it, compared to bacteria, is the fact, that it produces just acid L(+). However, the fermentation mode is aerobic (high sterile air preparation requirements). The aerobic mode of filamentous fungi can be an advantage in the event of direct lactic acid calcium salts preparation, during which prolonging of fermentation and decreasing of yields can occur as a result of inefficient neutralization (weak stirring) in the case of calcium carbonate (Mattey M.: *Critical Reviews in Biotechnology* 12, 87-132, 1992).

The advantage of bacterial fermentation is its anaerobic mode, hence the simplicity of cultivating devices and lower sterility requirements. Bacteria of the genus *Lactobacillus*, which convert a sucrose substrate (glucose, sucrose, lactose) at the temperature of 30° C. to 40° C. into lactic acid with different L(+)-, D(−)- and DL acid form content according to properties of the producer, are primarily used for industrial production.

The immobilization of microorganisms by encapsulation into gel carriers is one of the methods, which provide the biomass concentrating in a reactor without a biomass growth in a thoroughly fermented medium. This method consists of enclosing cells into capsules of natural or synthetic gels. The cells must be bigger than the pores of the carrier so that cell release does not occur, while simultaneously ensuring the free diffusion of a substrate and products to the encapsulated cells.

Immobilization of lactic bacteria into different carriers is currently known. Above all, these are carageenans, pectates, alginates of the natural gels (Norton, S. et al.: *Enzyme Microbial Technol* 16, 457-466, 1994; Richter, K. et al.: *Acta Biotechnol.* 11, 229-341, 1991; Yan, J. et al.: *Chem. Biochem. Eng. Q*: 15 (2), 59-63, 2001) and polyacrylamide of the synthetic carriers (Tuli, A. et al.: *Enzyme Microbial Technol.* 7, 164-168, 1985). The immobilizates are produced in the form of balls with diameter from 3 mm to 5 mm, usually by dropping the relevant gel into a hardening solution. However, the disadvantage of such methods is that the ball-shaped form of the immobilizates causes diffusion limitations inside the balls. The whole gel volume is not used and as a consequence, the microorganisms only grow just under the surface of the ball.

Another suitable method of immobilization is lactic bacteria encapsulation into a polyvinyl alcohol gel. This has numerous advantages compared to other carriers. First of all it is cheap, nontoxic for microorganisms, hardly biodegradable, has excellent physical-mechanical properties, there are no side effects on microorganisms and it shows long term stability (Pat DE 198 27 552.8). Furthermore, the immobilization of cells by the method according to the above mentioned invention is considerate to the productive microorganism (assures a high viability of the microorganism after immobilization and a high rate of surviving microorganisms after immobilization procedure), because the cross-linking of the matrix occurs in a stream of drying air and thus replaces the currently used procedures of cross-linking by freezing (Pat. DE 43 27 923) or hardening in a system with boric acid (U.S. Pat. No. 5,290,693). Furthermore, the lens-shaped form of immobilizates assures optimal loading of the whole volume of the carrier for the growth of microorganisms and the production of lactic acid. The immobilizates prepared by this method can be used repeatedly in batch, semi continual and continual fermentation operation modes.

It is generally known that yeasts *Saccharomyces cerevisiae* or other yeast microorganisms, which are able to convert glucose and other saccharides into ethanol during the process of fermentation, are traditionally used for the production of ethanol. This fermentation is the basis of beer and wine production but also the foundation of ethanol production for industrial, food and fuel purposes. Recently, growing interest in technologies using bacteria as producers of ethanol has been noticed. *Zymomonas mobilis* is one of the bacterial producers of ethanol. It is a gram-negative facultatively anaerobic microorganism. It has several advantages compared to yeasts: faster growth of biomass (but generally lower biomass production), higher specific rates of substrate utilization and product creation, it does not need a monitored oxygen supply and produces less side metabolites. It metabolizes glucose and fructose by the Entner-Doudoroff path, which usually occurs with anaerobic microorganisms. In this metabolic path one mole of glucose is converted into 2 moles of ethanol, 2 moles of $CO_2$ and one mole of ATP. This metabolic path minimizes the amount of glucose changed into biomass and in that way increases the ethanol production. The real yield (g alcohol/g glucose) is raised to 0.49 with bacteria, and is usually 0.44 with yeasts).

Fermentation with the assistance of free *Zymomonas mobilis* cells can occur in batch, semi continual and also continual operation modes (Rogers P. L., Tribe D. E.: U.S. Pat. No. 4,403,034; Rogers P. L., et al., U.S. Pat. No. 4,443,543; Salzbrunn W., et al., U.S. Pat. No. 4,876,196; Bu'lock J. D., Pat GB 2075053).

To date, research interest has focused on the increase of microorganism productivity and on modifying the arrangement of fermentation devices with various innovations; for example cell recycling, the use of flocculating microorganisms and etc. (Arcuri E. J., et al., U.S. Pat. No. 4,413,058; Rogers P. L., et al., U.S. Pat. No. 4,443,544).

The fermentation product (ethanol) is accumulated in a liquid medium and is isolated almost entirely by distillation. It is desirable during product isolation to reduce considerably the content of biomass by sedimentation, centrifuging, filtration and the like, without regard to the arrangement and the technology used. Elevated insoluble content increases distillation energy requirements, causes technological problems (fouling of the distilling apparatus, foaming etc), increases maintenance requirements and can also influence product quality. On the other hand, maximum efficiency of ethanol production must be achieved. The ethanol production rate is directly proportional to the amount of biomass in a fermentor. It means that with constant conditions, increased biomass content causes shortening of the time needed for production of a given amount of ethanol. One of the methods, enabling biomass concentration in a reactor without biomass growth in a thoroughly fermented medium, is microorganism immobilization by encapsulation in gel carriers. This method is based on cells encapsulation into natural or synthetic gel capsules. The cells size must be bigger than the pores size of a carrier so that cell release did not occur, but simultaneously free diffusion of a substrate and products to the encapsulated cells was ensured.

Immobilization of the bacteria genus *Zymomonas* in various carriers is currently known. Above all, these are carageenans and alginates of the natural gels (Cheetham P. S. J., U.S. Pat. No. 4,393,136; Chibata I., U.S. Pat. No. 4,350,765; Kikuta M., U.S. Pat. No. 5,990,191; Yamada T., et al., U.S. Pat. No. 4,680,263) and polyacrylamide of the synthetic carriers (Yamada T., et al., U.S. Pat. No. 4,680,263; Cheetham P. S. J., U.S. Pat. No. 4,393,136). The immobilizates are usually produced in the form of balls with diameter from 3 mm to 5 mm, mostly by dropping the relevant gel into a hardening solution. However, the disadvantage of such method is that the ball-shaped form of immobilizates causes diffusion limitations inside the balls. The whole gel volume is not used for cell loading and consequently, the microorganism only grows just beneath the surface of a carrier-ball, and does not load the whole volume of the matrix.

A suitable immobilization method is encapsulation the bacterium *Zymomonas mobilis* into polyvinyl alcohol gel. This has a number of advantages compared to the other carriers. First of all, it is cheap, nontoxic for microorganism, hardly biodegradable, has excellent physical-mechanical properties, there are no side effects on the microorganism and it shows long term stability (Pat. DE 198 27 552.8). Furthermore, the immobilization of cells by the method according to the above mentioned invention is considerate to the productive microorganism (assures a high viability of the microorganism after immobilization and a high rate of surviving microorganisms after immobilization), because the cross-linking of the matrix occurs in a stream of drying air and thus replaces the currently used procedures of cross-linking by freezing (Pat. DE 43 27 923) or hardening in a system with boric acid (U.S. Pat. No. 5,290,693). Furthermore, the lenticular shape of the immobilizates assures optimum utilization of the whole volume of the carrier for the growth of microorganisms and the production of ethanol. The immobilizates prepared by this method can be used repeatedly in batch, semi continual and continual fermentation modes.

Using ball-shaped form of immobilizates, ethanol production was 77 $mg_{ethanol}/ml_{gel}/h$ with the aid of *Zymomonas mobilis* immobilized into carageenan, with 10% by weight of the glucose medium, in a 500 ml batch reactor filled with 20 ml of immobilizates with an immobilizates diameter of 4 mm and a temperature of 30° C., (Chibata I., U.S. Pat. No. 4,350, 765). When the producer was immobilized into sodium alginate, where wet cell weight in the immobilizates comprised 20% ww/v (ww—wet cell weight, corresponds to ⅕ of dry cell weight), the productivity under the same conditions was 0.49 $g_{ethanol}/g_{ww}/h$ in the batch system, which after recalculation corresponds to 98 $mg_{ethanol}/ml_{gel}/h$, and in the continual mode 0.47 $g_{ethanol}/g_{ww}/h$, which after digit recalculation corresponds to 94 $mg_{ethanol}/ml_{gel}/h$ (Cheetham P. S. J., U.S. Pat. No. 4,393,136).

An alternative use of a gel carrier in biotechnology processes is in the method of producing glucose and fructose from sucrose by the help of immobilized enzyme invertase. Sucrose is a storage disaccharide present mainly in sugar beet and sugar cane. It is used in the food industry and also as a substrate in fermentation processes. It is composed of the monosaccharide glucose and fructose. Sucrose provides these monosaccharides by means of hydrolysis, for example by enzymatic hydrolysis using the enzyme invertase. Its use results in the creation of a mixture of glucose and fructose (invert sugar) which, compared to non-hydrolyzed sucrose, brings a number of advantages: decreased production of crystal turbidity, increased sweetness and usability in fermentation processes.

In industrial practice, enzyme preparations of invertase, which are not recyclable, are used for sucrose hydrolysis. That is the reason why the enzyme becomes one of the biggest economic items in the production of glucose-fructose sirups. Suitable immobilization method of this enzyme provides multiple use of it, and furthermore, it is possible to make the whole production process continuous and by that remarkably increase its effectiveness. The most frequently used technique is cross-linking. The most commonly used cross-linking agents are polyamide (Sou M. et al. JP58086085, Rohrbach R. P. et al. U.S. Pat. No. 426,842), glutaraldehyde (Lee D. M et al. U.S. Pat. No. 4,749,653), polymers with uncombined carboxyl groups (Mauz O. U.S. Pat. No. 4,767,620), polymers with epoxide groups (Mauz O. U.S. Pat. No. 4,931,476), immobilization into foto cross-linking bitumens (Kunihiro I. JP55023941) and embedment on various matrixes by the help of a cross-linking agent, such as immobilization on glass balls by the help of glutaraldehyde. (Toshiyuki Y. et al. JP58179494). Other methods are the covalent attachment of invertase on silica gel particles by the help of glutaraldehyde (Thibauit P. A. EP 0231668), covalent bonding by the help of disulphide bonds on organic and inorganic carriers (Cormier R. A. et al. U.S. Pat. No. 4,176,006), covalent binding by the help of organosilane (Ho G. H. et al. U.S. Pat. No. 4,384,045), covalent binding by the help of dialdehyde on cellulose and lignine materials (Monsan P. U.S. Pat. No. 4,405,715) and covalent binding on dialkylaminoalkyl cellulose (Lapins Ch. D. et al. U.S. Pat. No. 4,933,284). The invertase was also immobilized by adsorption; for example on a matrix from animal bones (Findlay Ch. J. U.S. Pat. No. 5,037,749). Another method is encapsulating cell lysates with high invertase activity into alginate gel (Obana H. et al. JP 57163484, Chang H. N. et al. U.S. Pat. No. 5,766,907) or into polyurethane polymers (Hartdegen F. J. et al. U.S. Pat. No. 4,098,645). Combined techniques, such as for example adsorption of an enzyme on cotton treated by polyethylenimine and subsequent cross-linking by glutaraldehyde (Yamazaki H. et al. CA1203187) also have practical usage.

The use of PVA (polyvinyl alcohol gel) appears to be a very good alternative. The invertase was successfully immobilized into a carrier with a solid center covered by PVA gel (Yamamoto H. and koet al. JP2005042037). Foto cross-linking PVA mixed with polyethylene glycol was also used for covalent binding and invertase enclosing (Ichimura K. JP 58152483, Suehiro T. et al. JP 1252285, Izumida H. et al. JP 1071491). A PVA matrix can also be cross-linked by boric acid, whereas the invertase is encapsulated into the gel (Guocheng Ch. et al. CN 1076488), or by drying (Ishimura F et al. U.S. Pat. No. 4,727,030). Other methods have also been used combined with cross-linking (Tsutsumi S. et al. JP 2046288), or with the addition of vinyl acetate (Moriya T. et al., JP 56113290), vinyl amine (Moriya T. et al., JP 56113292), or aminoacetalized PVA (Yamauchi A. et al. U.S. Pat. No. 4,307,151).

An alternative use of a gel carrier in biotechnological processes is in the method of glucose production from starch by the help of immobilized glucoamylase enzyme. Starch, the nutritive storage matter of plants, is one of the main sources of glucose in food industry and also in the fermentation industry. Starch comprises two types of molecules: amylase and amylopectin. Amylase, in corn for example, represents 10% of total starch. It comprises up to 1 000 glucose units, linked by α-1,4-glycoside bonds. The remaining 90% represents amylopectin in which, apart from α-1,4-glycoside bonds, α-1,6-glycoside bonds are also included. The number of glucose units in the chain is up to 10 000.

The process of starch raw material pretreatment for usage in fermentation processes consists of two steps. In the first step, starch liquefaction comes about by the help of endoenzyme α-amylase, which randomly dissociates α-1,4-glycoside bonds at a high temperature. This reaction causes the formation of dextrins and lower oligosaccharides with different chain lengths.

In the second step, dextrins and oligosaccharides are dissociated from the non-reducing end by exoenzyme glucoamylase into glucose units. Glucoamylase dissociates both α-1,4-, and α-1,6-glycoside bonds. However, α-1,6-glycoside bonds are hydrolyzed at a much lower rate. The rate of the hydrolysis also depends on the chain length.

In industrial practice, from 1 l to 1.2 l of glucoamylase enzyme preparation, which is not recyclable, is used per tonne of starch. Suitable immobilization of that enzyme would allow its multiple use, with the possibility of making the whole process continual. Significant improvement has been achieved with immobilization of this enzyme by cross-linking with an agent, such as polyamine (Symon et al. U.S. Pat. No. 4,415,663, Lantero et al. U.S. Pat. No. 5,472,861, DeFilippi U.S. Pat. No. 4,343,901, Rohrbach et al. U.S. Pat. No. 4,268,423), glutaraldehyde (Lee et al. U.S. Pat. No. 4,749, 653, Nishimura et al. U.S. Pat. No. 4,888,285, Rorvah et al. K.R. 8601229), acryl or alyl agents (Boross et al. U.S. Pat. No. 4,794,083, Selemenev et al. RU 2204600), by means of which the enzyme is anchored on an inorganic or organic matrix. The usage of adsorption methods (Abdullah et al. U.S. Pat. No. 4,226,937, Kumakura et al. JP 61060700, Motai et al. J.P. 59232092, Selemenev et al. R.U. 2181770, Kimura et al. J.P. 63056297), and also membrane reactors with immobilized glucoamylase (Thomas et al. U.S. Pat. No. 5,130,237) appears to be suitable. Encapsulation, which biological material encapsulates into a gel structure and is used primarily for microorganism immobilization, is entirely absent during glucoamylase immobilization. However, without cross-linking into bigger structures the enzyme is easily washed out from matrix pores.

An alternative use of a gel carrier in biotechnology processes is in the method of lactose solution hydrolysis and the production of D-galactose, D-glucose and galactooligosaccharides from lactose solutions by the help of immobilized β-galactosidase.

Disaccharide lactose is synthesized in the mammary glands of most mammals. It is commercially produced from cows' milk (with a lactose content of 4.5% to 5% w.) by extraction from whey (Baldrick and Bamford, 1997). Lactose present in milk and milk products represents an important nutritional item. It supports the growth of *Bifidobacterium* sp., it is the source of galactose needed for the production of galactolipides and galactooligosaccharides, it helps in calcium absorption, etc. (Maldonado al., 1998). It has a low solubility and it crystallizes at a concentration of more than 18% w. That appears to be a problem, because the lactose crystals cause a disagreeable sand-like texture (Zadow, 1992)

in the production of dairy products, such as condensed milk and ice-cream. This is the reason why lactose hydrolysis is highly desirable for these products. Furthermore, lactose hydrolysis also causes a considerable decrease in the hygroscopicity of dried milk products, an increase in sweetness and the process of the Maillard reactions is reduced (Čurda et al., 2001, Zadow, 1992, Rosenberg et al., 1995).

β-galactosidase is not only significant in lactose hydrolysis in milk, but also in whey processing. Whey is produced in quite large amounts as a side product of the dairy industry during the production of cheese, cottage cheese and casein. During cheese production, more than 150 million tons of whey is produced annually in the world (on average, 10 l of whey per kg of cheese) and world-wide cheese production has been increasing constantly. Whey is still not extensively processed, which represents an economic and ecological problem (Novalin et al., 2005). Furthermore, the handling thereof entails many restrictions and it is not possible to freely release it into the environment. Half of the waste product produced is used in the production of whey protein concentrates (WPC), but primarily for feeding farm animals (Rudolfová and Čurda, 2005). Whey can be also used as a raw material for ethanol production. In consideration of this fact, it could be an attractive substrate for fermentation processes in the future (Coté et al., 2004). For example, during ethanol production it is possible to use *Kluyveromyces* yeast which utilizes lactose. Lactose hydrolysis enables the use of thickened whey with a higher concentration of C-source as a substrate and thereby considerably increases the fermentation yield (Rosenberg et al., 1995). In some cases it is possible to perform the fermentation process in such a way that the productive microorganism utilizes only the glucose present, while the remaining galactose can be isolated, purified or chemically modified afterwards (Rosenberg, 2000).

Another significant use of β-galactosidase in the food industry is the creation of galactooligosaccharides (GOS). They are simultaneously formed during lactose hydrolysis due to the transglycozylate activity of β-galactosidase. β-galactosidase transglycozylate activity was first described in the 1950's (Aronson, 1952). The first published works focused on monitoring the favorable effects of GOS and the search for optimal methods of their production (Mahoney, 1998).

GOS belongs to the group of so-called probiotics: indigestible food components which selectively stimulate the growth or, more precisely, the activity of probiotic cultures in the human digestive tract. Owing to their β-configuration, GOS are resistant to hydrolysis by saliva and digestive fluid enzymes, which hydrolysis β-glycoside bonds selectively (Sako et al., 1999). GOS pass into the large intestine, where they participate in many important processes. Bifidogenous microflora metabolizes GOS into short chain fatty acids (acetic, propionic, lactic and butyric acid) and into gases (Johnson et al., 1993). Incipient acids stimulate peristalsis of the intestine and aid the absorption of calcium and iron by decreasing pH. GOS are also known as *bifidobacterium* growth factors, which are recognized for their beneficial health effects. Furthermore, bifidobacteria selectively utilizes galactooligosaccharides, which suppresses the growth of undesirable microorganisms in the digestive tract (Pennisin, 1997). GOS are also beneficial for oral cavity health, when not utilized by oral micro flora (*Streptococcus mutants*), and thus prevent the formation of dental caries (Szilagyi, 1999).

The individual β-galactosidases differ in the total amount and structure of GOS produced. For example, after isolating β-galactosidases from different strains of *Bifidobacterium* genus and their subsequent use during GOS synthesis from a 30% lactose solution, there was an evident difference in the amount produced. In the case of *Bifidobacterium angulatum*, they formed 43.8% of all saccharides present in a solution, whilst in the case of *Bifidobacterium pseudolongum* it was only 26.8% (Rabiu et al., 2001). Regarding the structure, the type of the newly formed glycoside bond of two monosaccharide units (galactose-galactose, galactose-glucose) is in the case of *Bifidobacterium bifidum* β(1-3) (Dumortier et al., 1994), as opposed to β(1-4) in *Bacillus circulans* (Mozaffar et al., 1984) and β(1-6) in *Streptococcus thermophilus* (Matsumoto, 1990).

Enzyme, β-galactosidase was immobilized in the following ways: entrapment (Mammarella and Rubiolo, 2005, Rodriguez-Nogales and Delgadillo, 2005), cross-linking (Sungur and Akbulut, 1994), adsorption (Carpio et al., 2000), covalent binding (Hu et al., 1993, Findlay, 1991, Di Serio et al., 2003), enclosure in membranes (Novalin et al., 2005), or a combination of these methods (more closely described in part 1.2.1).

The β-galactosidase immobilization process is associated with certain disadvantages, such as the loss of enzyme activity after immobilization. The decrease of β-galactosidase activity after immobilization ranges from 5% to 90% and depends on the immobilization method used. This disadvantage is compensated by the possibility of reusability of an immobilizates. The ability to preserve an enzymes activity and the stability of an immobilizates during repeated usage are the decisive parameters for the application of an immobilizates on an industrial scale (Tanaka and Kawamoto, 1999).

Polyacrylamide and a polyvinyl alcohol gel are often used for the method of entrapment. A PVA matrix was also used for encapsulation of β-galactosidase isolated from filamentous fungi, whereby its temperature stability was increased. The enzyme retained 70% of its previous activity after 24 hours at 50° C. and 5% of its previous activity at 60° C. (Batsalova et al., 1987). Khare and Gupta (1988) immobilized β-galactosidase from *E. coli* using a combination of the two methods: cross-linking and subsequent encapsulation into a polyacrylamide gel. In the same procedure, but using dimethyladipimidate as a cross-linking agent and enzyme preventing substances: bovine serum albumin, cysteine and lactose, the activity measured 190% of the previous immobilizer activity. The comparison of different methods of β-galactosidase immobilization from thermophilic bacterium *Thermus aquaticus*, showed that cross-linking and subsequent entrapment into agarose granula is the preferable process for the immobilization of high concentrations of enzyme with the benefit of high enzyme activity (Berger et al., 1995). The process of immobilization enables increased enzyme stability under different reaction conditions. The entrapment of β-galactosidase from *A. oryzae* into porous PVA cryogel increased the temperature resistance of the enzyme, pH value and ionic strength (Rossi et al., 1999).

Adsorption is a technically undemanding method of immobilization. Hydrophobic cotton fiber can serve, for example, as a carrier on which an enzyme preserves 50% of its previous activity (Sharma and Yamazaki, 1984). Bakken et al., used β-galactosidase from *A. oryzae* by adsorbing it on polyvinylchloride and silica gel in the form of a membrane (1990) during lactose hydrolysis in milk in an axial flow reactor. β-galactosidase immobilized by adsorption on bone powder preserved 83% of its previous activity, but during four batch hydrolyses the immobilizates gradually lost its activity. After the fourth hydrolysis, the activity of the immobilizates was just 24% of the original (Carpio et al., 2000). This experiment showed the disadvantage of the immobilization method, during which slight desorption occurs. This effect can be eliminated by the addition of a suitable cross-linking agent (Szczodrak, 2000).

Piettaa et al. (1989) immobilized β-galactosidase isolated from *A. oryzae* into two different carriers using a covalent bond. The first was zeolite, but it was not convenient because it only binds a small amount of enzyme. Contrary to that, powder nylon-6 covalently bound a larger amount of the enzyme and created a stable complex. Peters and Rehm (2006) immobilized β-galactosidase by covalent binding onto polyhydroxyalkanoate granules. The immobilizates gained was stable in the long term during its storage under different conditions, which provides evidence of a strong bond between the carrier and the immobilized enzyme.

Glutardialdehyde with two reactive functional groups is the most frequently used cross-linking agent in β-galactosidase immobilization (Guisán et al., 1997, Szczodrak, 2000, Zhou and Chen 2, 2001). However, the method of cross-linking immobilization is particularly used in combination with other methods (above mentioned, Panesar et al., in press), such as adsorption or entrapment. For example β-galactosidase from *A. oryzae* immobilized using the entrapment method into the form of fibers composed from alginate and gelatine, was then cross-linked by glutardialdehyde, which prevented washing out of the enzyme (Tanriseven and Dogan, 2002). This type of cross-linking was also used in β-galactosidase immobilization into a cobalt-alginate gel. However, cobalt release during lactose hydrolysis made the use of the immobilizates impossible in the food industry (Ates and Mehmetoglu, 1997).

The activity and stability of the immobilized enzyme is affected by pH value, temperature and ionic strength (Roy and Gupta, 2003). Compared to a free enzyme, the immobilized enzyme has wider optimum pH and temperature ranges as mentioned in most published works. The higher stability of immobilized β-galactosidase at a lower pH value and higher temperature is an advantage in lactose hydrolysis, and furthermore, by decreasing the pH value and increasing the temperature the risk of contamination is reduced. On the other hand, the shift of the pH optimum and the stability increase is, under these conditions, an advantage during lactose hydrolysis in sweet whey, whose pH is within the 5.5 to 6.0 interval (Szczodrak, 2000).

β-galactosidase from different microbial sources was also immobilized for the purpose of production galactooligosaccharides in the continuous as well as in the batch operation mode (Chockchaisawasdee et al. 2005). Compared to a free enzyme, the immobilized enzyme produced lower GOS concentrations. This decrease was caused by the limitation of substrate access to the enzyme in the immobilized system (Mahoney, 1998). The concentration and structure of emerging GOS depended to considerable extent on the initial substrate concentration and on the origin of the enzyme. The increase in the initial lactose concentration from 14% to 23% doubled the GOS production (Foda and Lopez-Leiva, 2000, Chockchaisawasdee et al., 2005).

Shin et al. (1998) immobilized an enzyme isolated from *Bullera singularis* ATTC 24193 into chitozane granules. They used the thus immobilized enzyme in GOS production. The experiment lasted for 15 days, during which time they registered 55% w. of GOS of all saccharides (the initial substrate concentration being $100 \, g \cdot l^{-1}$) and volume productivity of $4.4 \, g \cdot l^{-1} \cdot h^{-1}$. Another example of immobilized β-galactosidase usage in oligosaccharides production was also described in the work of Albayrak and Yang (2002). They reached the maximum production 26% of weight of all saccharides (with a substrate concentration $400 \, g \cdot l^{-1}$) and the volume productivity $106 \, g \cdot l^{-1} \cdot h^{-1}$ by using an enzyme from *A. oryzae* immobilized on cotton fiber. Foda and Lopez-Leiva (2000) tested a membrane flow reactor with immobilized β-galactosidase for GOS preparation. They reached the highest production (31% of weight) by using whey treated by ultrafiltration with an initial lactose concentration of 20% w. Whey is a rich source of lactose; its usage in GOS production appears to be very attractive.

There is a known casting unit which is used in the production of immobilizates, which are products—biocatalysts on the basis of polyvinyl alcohol carrier—usually manufactured in the lens-shaped form or small belts. The mixture of polyvinyl alcohol gel and biomass is applied to a continuous conveyor belt using a dropping, casting mechanism in accurate and previously defined dosages, where it is changed into an adhesive mass by drying and physically gelation during the production process. At present, the casting unit for the production of immobilizates based on a polyvinyl alcohol carrier consists of a casting mechanism arranged in front of the drying channel, inside which a continuous conveyor belt (made from polyethylene, for example) runs. The casting mechanism, known as a casting head, is fitted with one row of casting needle injectors with a diameter varying from 0.1 mm to 2.00 mm, which pulsate by the help of electromagnets with different frequency and different pulse length and transfer or pour the mixture of polyvinyl alcohol gel and biomass on the continuous conveyor belt. The casting unit further contains a reswelling section placed in the upper part of the drying channel, which is formed by a system of low-pressure spraying jets, which wets (reswell) the dried product. Furthermore, the casting unit is equipped with a collecting part, comprising of a pressure wiper made from stainless steel plate rinsed by spraying jets placed above the pressure stainless steel wiper and mounted on the carrying frame of the casting unit, above the drive cylinder of the belt. Ambient or dehumidified air are used as the source of drying media using continuous atmospheric dehumidification or continual freezing, which is warmed up by heating elements before entering the drying channel, and which ensures gelation by drying the immobilizates produced on the basis of a polyvinyl alcohol carrier. Casting units arranged in this manner are incapable of long-term economic production, in particular due to the difficulty in removing the immobilizates on the base of the polyvinyl alcohol carrier from the conveyor belt. A mechanical stainless steel wiper is used for wiping, and following collection. The wiper is firmly pressed against the surface of the conveyor belt, i.e. on the basis of elasticity, and subsequently, the mass is wiped off by the wiper and falls off into a collecting reservoir. This mechanical removal of the product from the belt is far from perfect, particularly considering the formation of big clusters, agglomerates of polyvinyl alcohol carrier, and the consequent production of a product with low or zero activity. A further disadvantage is also considerable mechanical wear of the casting unit's continuous conveyor belt. It was further learned, that the use of salt solutions in the reswelling part of the casting unit causes salts to cling to the surface of the continuous belt and consequently changes to the surface tension of the casting unit's the conveyor belt, hence the change in the shape of the product. This change means that during the removal and unsticking of the immobilizates from the conveyor belt damage and the formation of large clusters or agglomerates is unavoidable in most cases.

SUMMARY OF THE INVENTION

The above mentioned flaws are eliminated by the method for the industrial production of biocatalysts, with biologically active material in the form of immobilized enzymes or microorganisms which are immobilized into a polyvinyl alcohol gel, and by their use based on the fact, that for their industry production active biological material is used, which consist of the mixture containing free native, or pretreated (aggregated) enzyme catalyst, or productive microorganism, or their parts and a polyvinyl alcohol gel, afterwards the mixture is shaped and gelated in a drying air stream, at the temperature from 80° C. to 15° C. considering the biologically active material extent and keeping the geometrical ratio of the surface to the volume bigger than 7 mm$^{-1}$, and than so produced biocatalysts can be cultivated and afterwards used in biotechnological processes, in the conditions, which keep higher productivity, higher productive and enzymatic stability, long-term and repetitive use or definable controlling of the process with subsequent easy biocatalyst separation, to the given biotechnological process.

Main advantages of the technologies with immobilized cells are: the considerable reduction of the given process operating cost, associated with the possibility to use the biocatalyst repeatedly and to make the process continuous, keeping of the high concentration of fixed biomass in the system, and the lower costs of biomass separation and product isolation. If the process is made continuous, no biomass washing out from a carrier matrix occurs, the nonproductive growth phases are reduced, yields increase and higher reaction rates are achieved. It is also advantageous, that the biotechnological process controlling method according to this invention results in the reduction of the reaction volumes and the reaction intervals needed, which means decreasing in the operation costs and investments.

It is desirable for intensification of the current processes of nitrogen compounds removal from potable, industrial and waste waters in the form of gaseous nitrogen, by means of immobilized cells, to use a lens-shaped form of carrier, or more precisely the carrier in the shape of cylinder, height of which is four times up to twenty times lower than the bottom radius, or in the shape of a small belt, or more precisely a block, one of the dimensions of which is four times up to twenty times lower than the other two ones, so that the ratio (geometrical) of the surface to the volume (S/V) of the carrier is bigger than 7 mm$^{-1}$.

It is useful for the preparation of the biocatalyst, destined to remove nitrogen pollution from potable, industrial and waste waters, to encapsulate nitrifying and denitrifying bacteria into a polyvinyl alcohol gel, and then to gelate and shape the mixture of a polyvinyl alcohol carrier and bacterial cells by drying into the lens-shaped or small belt form at the temperature of 80° C. to 15° C., so that the ratio of the surface to the volume of the biocatalysts is minimally 7.0 mm$^{-1}$, and then to harden immobilizates in a suitable sodium sulphate solution. The immobilizates are then cultivated in a water nutrient medium containing from 10 mg/l to 1000 mg/l of N—NH$_4$ and from 10 mg/l to 1500 mg/l N—NO$_3$ of nitrogenous substrate at the temperature from 20° C. to 35° C. and the pH value from 6.0 to 9.5.

The nitrifying bacteria containing biocatalyst is prepared apart from the denitrifying bacteria containing biocatalyst. Following cultivation of the biomass containing both biocatalysts can run directly in the industrial devices designated for nitrification and denitrification.

Pure mixed culture of nitrifying bacteria (*Nitrosomonas europeae* and *Nitrobacter winogradskiy*), is used for the immobilizates preparation by the help of encapsulation into PVA matrix. The used litotrophy bacteria (slowly growing organisms) get energy for their existence from nitrogen from ammonia (N—NH$_3$) oxidation, in case of *Nitrosomonas europeae* bacteria and from the nitrites (N—NO$_2$) oxidation in case of *Nitrobacter winogradskiy*.

Denitrifying bacteria (*Paraccocus denitrificans*), using nitrogen from nitrates (N—NO$_3$) as an electron acceptor instead of oxygen are used for the immobilizates preparation by the help of encapsulation into a PVA matrix. The denitrifying bacteria are organotrophy bacteria, which need organic carbon for their growth. The used cultivating solutions and some real industrial wastewater do not contain any organic agents and so it is necessary to add organic carbon—alcohols, saccharides and so on, preferably methanol, because it is cheap but produces relatively little biomass.

It is also useful, that the lens-shaped form of immobilizates keeps the optimal use of the whole gel carrier volume (cell loading) for the growth of microorganism, and thereby the optimal use of productive enzymatic properties of microorganisms and enzymes, which can be seen in the increased specific productivity of the biotechnological process using polyvinyl alcohol (PVA) immobilizates. This way prepared biocatalysts can be used repeatedly in the batch, semi continual and continual fermentation operation mode.

It is useful for the preparation of the biocatalyst, destined to ethanol production from saccharide substrates, to encapsulate the anaerobic bacteria *Zymomonas mobilis* into a polyvinyl alcohol gel, and then to gelate and shape the mixture of polyvinyl alcohol carrier and bacteria *Zymomonas* cells by drying at the temperature of 80° C. to 15° C., and then to cultivate the immobilizates in a water culture medium containing from 2% to 25% of weight of the saccharide substrate at the temperature of 20° C. to 40° C., and pH from 3.5 to 7.0, in ethanol presence, in the range from 1% to 15% of weight. It is also useful in this process that immobilized cells are separated from the liquid part and used repeatedly for the ethanol production, after the production is finished. Thus prepared biocatalysts can be used repeatedly in batch, semi continual and continual fermentation operation mode.

It is useful for the preparation of the biocatalyst, destined to the lactic acid production from saccharide substrates, to encapsulate thermophilic bacteria *Bacillus coagulans* into a polyvinyl alcohol gel, and then to gelate and shape the mixture of polyvinyl alcohol carrier and *Bacillus coagulans* bacterial cells by means of drying at the temperature of 80° C. to 15° C., at the ratio of the surface to the volume of the immobilizates bigger than 7.0 mm$^{-1}$, and then to cultivate the immobilized cells in a water culture medium containing from 2% to 14% of weight of saccharide substrate, at the temperature of 30° C. to 60° C., and pH value from 5.0 to 7.5, in lactic acid or its salts presence in the range from 1% to 12% w. It is also useful that the immobilized cells are separated from the liquid part and used repeatedly for the lactic acid production, after the production is finished. Thus prepared biocatalysts can be used repeatedly in batch, semi continual and continual fermentation mode.

It is useful to use *Bacillus coagulans* CCM 4318 strain for the increase of the lactic acid production productivity. That bacterial strain itself is characterized in the high productivity of lactic acid production, and considering the biocatalyst extent while conserving the ratio of its volume to its surface minimally 7.0 mm$^{-1}$, its lactic acid production productivity is even higher.

It is useful for the preparation of the biocatalyst, destined to the invert saccharide preparation from saccharide solutions, to encapsulate enzyme invertase into a polyvinyl alcohol gel, and then to gelate and shape the mixture of polyvinyl alcohol carrier and enzyme by drying at the temperature of 80° C. to 15° C. and at the ratio of the surface to the volume of the immobilizates minimally 7.0 mm$^{-1}$, and to use thus prepared enzyme for hydrolysis of the saccharide solutions, which contain from 2% to 50% of weight of saccharide substrate, at the temperature of 20° C. to 50° C. and pH value 3.5 to 7.0.

It is useful to separate the immobilized invertase from the liquid part, after hydrolysis is finished, and use it repeatedly in the invert sucrose production, the sucrose hydrolysis by means of immobilized invertase is performed in batch, semi continual and continual mode.

The present method for the invertase immobilization into the polyvinyl alcohol gel (PVA) is based on gel drying in a drying air stream, at the temperature of 80° C. to 15° C., whilst the interaction between the gel and invertase functional groups can occur. The lens-shape form of the immobilizates, in case the ratio of the surface to the volume of the immobilizate is minimally 7.0 $mm^{-1}$, secures the optimal use of the whole gel volume and the achievement of the high specific activities of the invertase. Thus immobilized enzyme is not washed out from the matrix and can be used in batch, semi continual and continual operation mode. It is useful for the preparation of the biocatalyst, destined to the D-glucose preparation from high saccharides, to encapsulate the glucoamylase enzyme into a polyvinyl alcohol gel and then to gelate and shape the mixture of polyvinyl alcohol carrier and enzyme by drying at the temperature of 80° C. to 15° C., and at the ratio of the surface to the volume of the immobilizates minimally 7.0 $mm^{-1}$, thus produced enzyme is used for hydrolysis of high saccharides, which are prepared by partial hydrolysis of a starch containing 2% to 40% of weight of the saccharide substrate at the temperature of 20° C. to 45° C. and pH value 3.5 to 7.

To prevent the washing glucoamylase out, it is useful to perform the enzyme immobilization into a polyvinyl alcohol gel (PVA) during the process of drying in air stream, at the temperature of 80° C. to 15° C., when the interactions between the gel functional groups and glucoamylase can occur. The enzyme immobilized by this method is not washed out from a matrix and can be used in batch, semi continual and continual mode. Thus prepared saccharide substrate, which contains glucose, can be used in fermentative and food industry.

It is also useful, that the immobilized glucoamylase is separated from liquid part, after hydrolysis is finished, and is used repeatedly in the glucose production.

It is also useful, that hydrolysis by means of immobilized glucoamylase is performed in batch, fed-batch and continual operation mode.

It is also useful, that the immobilized glucoamylase is used for the saccharification of the starch substrate in the ethanol fermentative production process.

It is also useful, that the immobilized glucoamylase is used for the saccharification of the starch substrate in the lactic acid fermentative production process.

It is useful for the biocatalyst preparation, destined to the lactose solutions hydrolysis, D-galactose, D-glucose and galactooligosaccharides preparation from the lactose solutions, to enclose enzyme β-galactosidase into a polyvinyl alcohol gel, and then to gelate and shape the mixture of polyvinyl alcohol carrier and enzyme by drying at the temperature of 80° C. to 15° C., and at the ratio of the surface to the volume of the immobilizates minimally 7.0 $mm^{-1}$, so the enzyme produced is used for the hydrolysis of the lactose solutions, which contain from 2% to 50% w. of saccharide substrate, at the temperature of 20° C. to 60° C. and pH value 3.0 to 7.0.

It is useful that the immobilized β-galactosidase, after the hydrolysis is finished, is separated from the liquid part and is used repeatedly for the D-galactose, D-glucose and galactooligosaccharide production, the lactose hydrolysis by means of immobilized β-galactosidase is performed in batch, fed-batch and continual operation mode.

A device for the preparation of the immobilized biocatalysts is the industrial production device, which provides an optimization of the volume and the surface of a biological carrier, in dependence on the extent of biologically active material, comprising a dropping, casting mechanism mounted in front of a drying channel, through which a continuous conveyor belt runs, wherein the device is equipped with at least one casting head with two rows of casting needle injectors connected to a tempered pressure tank and a compressor, the conveyor belt and a drying system—the source of a drying air, which is blown by means of ventilator into an air distribution system with incorporated heating elements, which runs into the upper drying channel, and further the lower final drying channel and a reswelling tank, between which a wiping and collecting device is mounted, designed on the basis of mechanical wiping and high-pressure rinse, which is connected to a pipeline with integrated high-pressure pump and low-pressure pump running into a collecting reservoir with cooling and further a rinse box for the continuous conveyor belt final cleaning by jets connected to a low-pressure pump, which is connected to a rinse tank by pipeline.

The device according to this invention forms a completely new assembly of an industrial casting device consisted of one or two casting heads, equipped with two rows of casting needle injectors, diameter of which is of 0.1 to 2.00 mm, which pulsate by means of electromagnets with the different frequency and pulse length, a conveyor belt with controlled drive, a drying channel with counter flow drying, the reswelling tank, an independent collecting low-pressure rinse system, and a lower drying channel with counter flow drying in the lower part of the casting device. It is also useful, that the independent system of high-pressure rinse by means of a water salt solution in the collecting reservoir, comprising the high-pressure pump for the pressure water delivery to the high-pressure jets, is the part of the device. Enhanced efficiency of the mechanic wiping of mass from the conveyor belt is achieved in this way.

It is also important, that the device of the present adjustment, and namely with this type of a collecting and rinse device, is able to secure the uninterrupted economic industrial immobilizates production based on the polyvinyl alcohol carrier.

It is useful for the errorless functioning of the wipable collecting device, which is the part of the casting device, if it is formed by a side frame, in which a mechanic polymer wiper providing the rinse at the angle from 45° to 80° is placed on a stainless pressure mechanism, with a spring pressure mechanism and the rinse by means of high-pressure jets system, fixed on the supporting stainless pipe distribution system, which is fixed in the frame, for the cleaning of inside and outside sides of the conveyor belt, there are the lower and the upper wipers with polymer brushes fixed behind the mechanic polymer wiper with the spring mechanism, and for final cleaning of the conveyor belt from the product in the place where it runs out of the frame, it is further provided with lower and upper wipers. It is also the advantage, that designed mechanism of the wipable collecting device cleans also the other side of the continuing conveyor belt, even in the case its inside surface is uneven, corrugated or rough.

The device according to this invention can be also used for wiping other adhesive stuff from the conveyor belt in productions of other adhesive materials.

BRIEF DESCRIPTION OF THE DRAWINGS

The invention will be closer illustrated by drawings, where.

DESCRIPTION OF RELATED TECHNOLOGY

Figure 1:
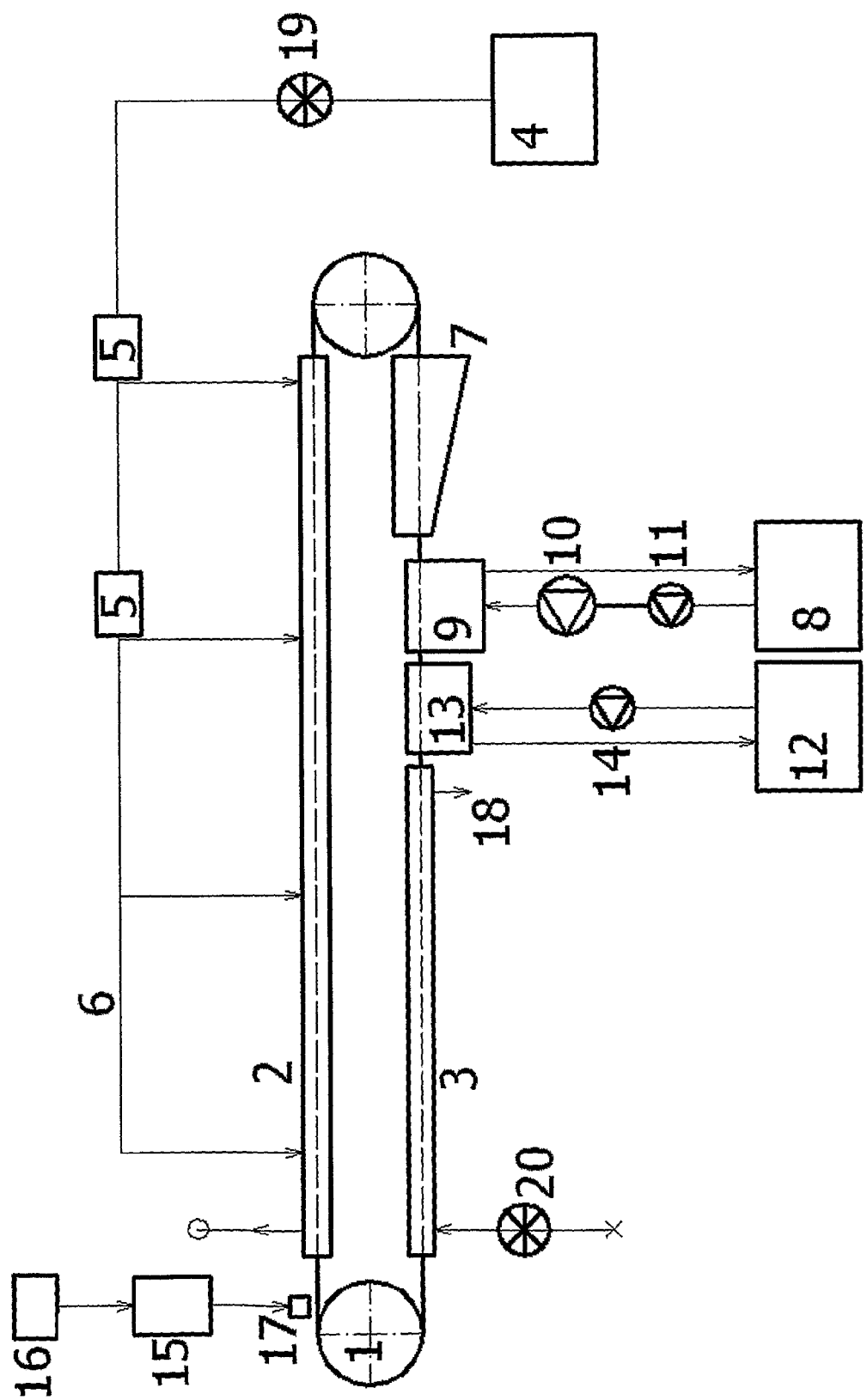
FIG. 1 illustrates the scheme of the casting machine, FIG. 2 the scheme of reswelling tank,
FIG. 3 the partial section of the collecting device and
FIG. 4 the scheme of the rinsing box.
Figure 2:
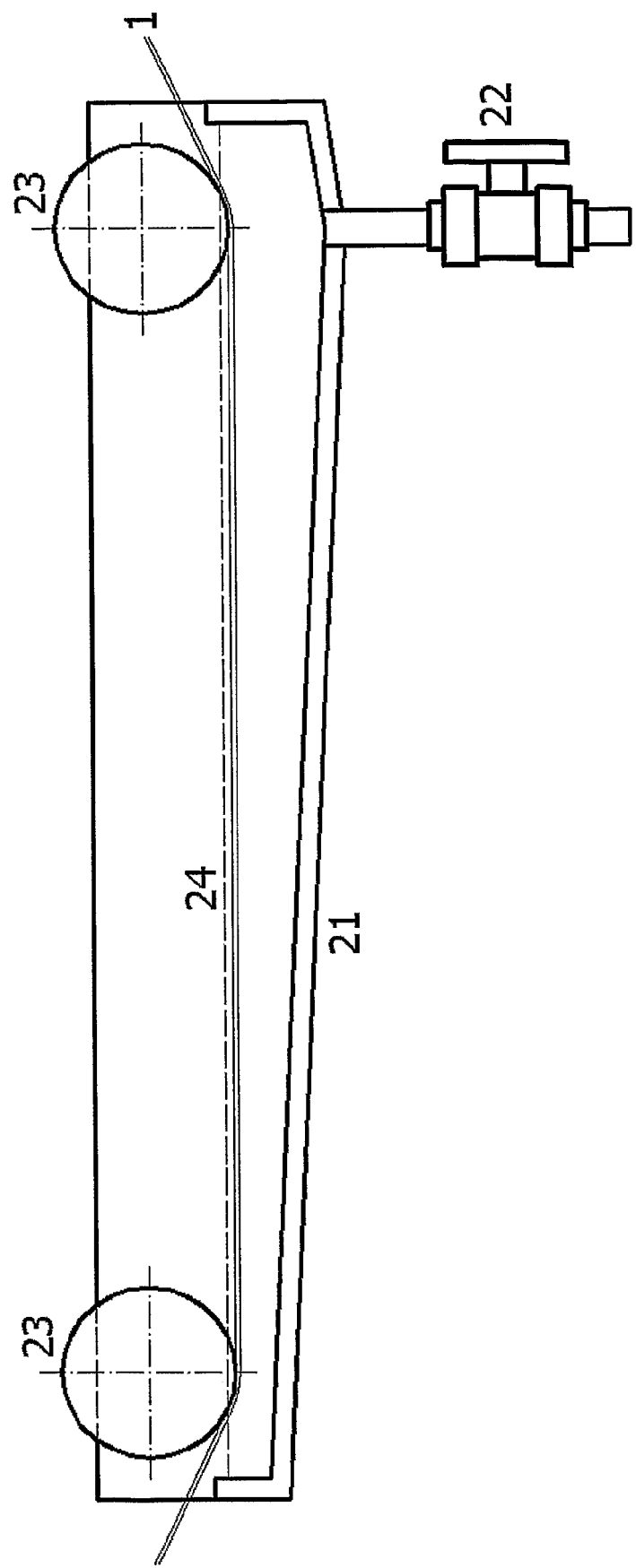
Figure 3:
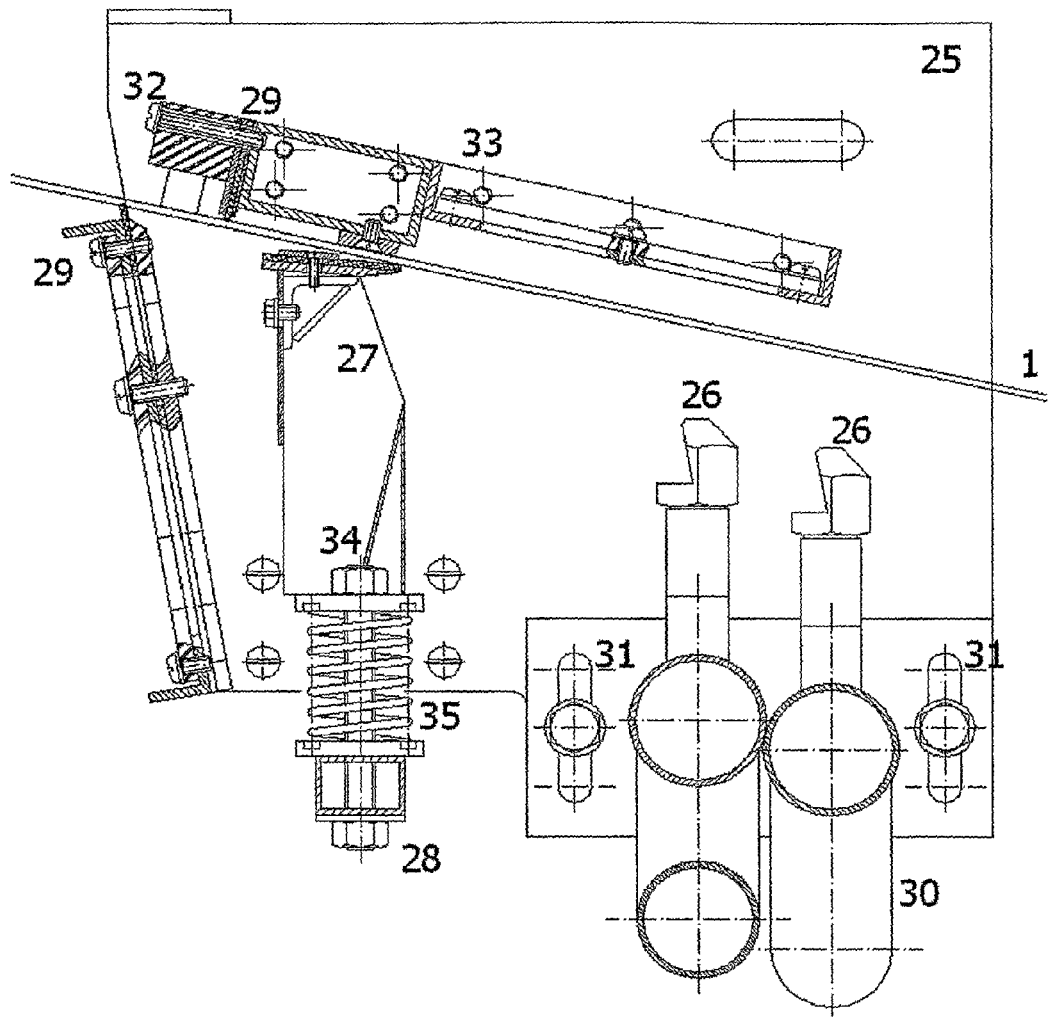
Figure 4:
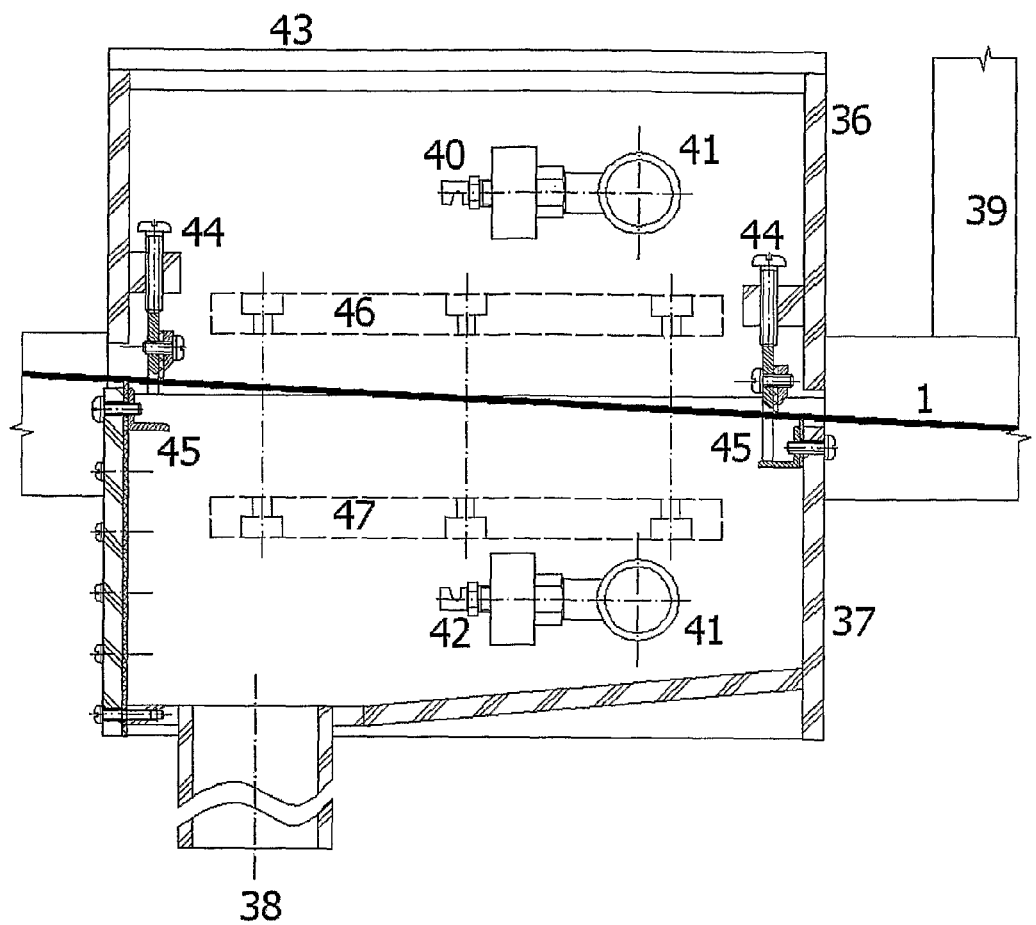

The method for the above mentioned carriers production and use in the process of nitrogen removal from waste waters by means of the immobilized nitrifying and denitrifying cells into a polyvinyl alcohol gel, will be described in the following examples.

EXAMPLE 1

Immobilizates—biocatalyst for the nitrification was prepared by the encapsulation of the nitrifying bacteria (*Nitrosomonas europeae* and *Nitrobacter winogradskiy*) pure mixed culture into PVA-hydrogel.

Immobilizates—biocatalyst for the denitrification was prepared by the encapsulation of denitrifying bacteria (*Paraccocus denitrificans*).

Immobilization was performed in this way: The solution of PVA, which contained 100 g of PVA (polyvinyl alcohol), 60 g of PEG (polyethyleneglycol), 790 g of distilled water, was prepared. 50 ml of the homogenous suspension of biomass was added into the thus prepared solution so that the resulting cell concentration was 0.60 g of the cells per 1 $dm^3$ of a gel. Thus prepared cell mixture in the PVA solution dropped onto a hard plate and then was cross-linked and shaped in a stream of dry air at the temperature of 80° C. to 15° C. Immobilizates, ratio of the surface to the volume of which was minimally 7 $mm^{-1}$, were then moved into the solution of sodium sulfate (0.01 mol/l) and ammonium chloride (0.1 mol/l) for 60 minutes. The immobilizates were cultivated or stored in a store medium at the temperature of 4° C., after the filtration.

In the case of nitrifying microorganisms, the batch cultivation performed in a water culture medium with the gradually increasing content of the nitrogen substrate 50 mg/l to 500 mg/l of N—$NH_4$, during which the cultivation of bacteria occurred at pH 7.0 and the dissolved oxygen concentration bigger than 1.5 mg/l.

In the case of denitrifying microorganisms, the batch cultivation performed in a water culture medium, with the content of nitrogen substrate 200 mg/l of N—$NO_3$ and other nutrients, at the temperature of 20° C. to 35° C. and pH 7.8 in presence of methanol as a C-substrate. The content of biomass in both biocatalysts was about 60 mg to 80 mg of a biomass dry matter per 1000 ml of PVA, after the cultivations.

So the immobilizates prepared underwent the repetitive batch fermentations. The nitrification (nitrogen from ammonia removal) in the reactor with the effective volume of 17 l, with the content of 15 l of synthetic waste water (WW), containing about 800 mg/l of N—$NH_4$ and 2000 g of the biocatalyst with encapsulated nitrifying bacteria was finished after 4 hours, which presents the nitrification rate about 1500 mg of N—$NH_4$/hr×kg of the biocatalyst, respective about 4.8 kg of N—$NH_4/m^3$ of WW×day and 36 kg of N—$NH_4/m^3$ of the biocatalyst×day.

The denitrification (nitrogen from nitrates removal) in the reactor with the 15.8 l effective volume, with the 15 l content of synthetic waste water with the concentration of 800 mg/l of N—$NO_3$ and 800 g of the biocatalyst with encapsulated nitrifying bacteria, was finished after 3 hours in the presence of methanol as a C-substrate, which presents the denitrification rate of about 2000 mg of N—$NO_3$/hr×kg of the biocatalyst, respective about 6 kg of N—$NO_3/m^3$ of WW×day and 45 kg of N—$NO_3/m^3$ of the biocatalyst×day.

EXAMPLE 2

The immobilizates prepared and cultivated, as described above in Example 1, were used for the nitrogen pollution removal from real waste water with the high nitrogen pollution concentration 200 mg/l to 1000 mg/l of N—$NH_4$ and in fact zero dichromate value, in the continual adjustment of nitrification and denitrification.

The continual model unit was used for testing the simultaneous nitrification and denitrification, where the effective volume of the stirring nitrifying reactor was 17 l and the effective volume in the stirring denitrifying reactor was 3.8 l. The flow rate of the real industrial waste water was 35 l/day with the content of about 1600 mg/l of N—$NH_4$.

2000 g of the biocatalyst with encapsulated nitrifying bacteria was added into the nitrifying reactor. 800 g of the biocatalyst with encapsulated denitrifying bacteria was added into the denitrifying reactor.

The average nitrification rate of about 1000 mg of N—$NH_4$/hr×kg of the biocatalyst at 95% nitrification efficiency, and the average denitrification rate in presence of methanol as the C-substrate about 1600 mg of N—$NO_3$/hr× kg of the biocatalyst, was achieved during the several-week experiment. The nitrogen pollution removal rate was about 1.5 $kg/m^3$ of WW×day.

EXAMPLE 3

The immobilizates, prepared and cultivated as described above in Example 1, were used in the nitrogen pollution removal from real waste water with the high content of nitrogen pollution 200 mg/l to 1000 mg/l of N—$NH_4$ and high dichromate value (> 1000 mg/l) in the continual nitrification and denitrification adjustment.

Thus prepared immobilizates underwent batch fermentations. The nitrification (nitrogen from ammonia removal) in the reactor with the 17 l effective volume, with the 15 l content of synthetic waste water (WW) with the content of about 800 mg/l of N—$NH_4$ and 2000 g of the biocatalyst with encapsulated nitrifying bacteria, was finished after 12 hours, which presents the nitrification rate of about 500 mg of N—$NH_4$/hr×kg of the biocatalyst, respective about 1.6 kg of N—$NH_4/m^3$ of WW×day and 12 kg of N—$NH_4/m^3$ of the biocatalyst× day.

The denitrification (nitrous nitrogen removal) in the reactor with the effective volume of 15.8 l, with 15 l content of synthetic waste water with the concentration of 800 mg/l of N—$NO_3$ and 800 g of the biocatalyst with encapsulated nitrifying bacteria, was finished after 6 hours in the presence of methanol as C-substrate, which presents denitrification rate about 1000 mg of N—$NO_3$/hod×kg of the biocatalyst, respective about 3 kg of N—$NO_3/m^3$ of WW×day and 22.5 kg of N—$NO_3/m^3$ of the biocatalyst×day.

The method for the production and use of the above mentioned carriers in the lactic acid production from saccharide substrates by means of the *Bacillus coagulans* immobilized cells into a polyvinyl alcohol gel will be illustrated in the following examples.

EXAMPLE 4

The *Bacillus coagulans* CCM 4318 spore suspension was prepared by inoculating with 0.2 $cm^3$ from the storage culture on the surface of the MRS agar with sterile $CaCO_3$ (3 h, 160°

C.) in P. dishes (Ø9 cm). The incubation run for 72 h at the temperature of 50° C. in the laboratory thermostat. Then the sporulated culture was overlaid by 5 cm³ of sterile distilled water and moved into the Erlenmayer flask. So the suspension obtained was incubated for 25 min at the temperature of 70° C. and then used in the immobilization into the polyvinyl alcohol (PVA) gel.

The PVA solution was prepared, which contained 100 g of PVA (polyvinyl alcohol), 60 g of PEG (polyethylene glycol) and 790 g of distilled water. 50 ml of the homogenous biomass suspension was added into thus prepared solution so that the final cell concentration was 0.67 g of cells (dry matter) per 1 dm³ of a gel. Thus prepared cell mixture in the PVA solution dropped onto a hard plate and then was cross-linked and shaped in a stream of dry air at the temperature gradient: from 80° C. to 15° C. The immobilizates, the ratio of the surface to the volume of which was minimally 7 mm$^{-1}$, were then moved into the sodium sulfate solution (0, 1 mol/l) for 60 minutes. The immobilizates were used in the batch fermentations or stored in sterile tap water at the temperature of 4° C., after the filtration.

The biomass propagation was performed in the repetitive batch fermentations in 5 l laboratory fermentor with 2.6 l of production medium. The production medium contained 60 g of saccharose, 10 g of yeast extract, 1 g of $(NH_4)_2HPO_4$, 0.2 g of $MgSO_4 \times 7H_2O$, 0.05 g of $MnSO_4 \times 4H_2O$, 0.01 g of $FeSO_4 \times 7H_2O$ in 1 l of distilled water. The production medium was boiled for the short time, cooled to the temperature of 60° C. and then 400 g of the wet immobilizates was added. The temperature was gradually lowered to 45° C. during 1 hour, pH lowered spontaneously from 6.9 to 5.0 and then was kept at 5.8 during the following fermentation by adding of the 26% ammoniac water solution. The fermentation was performed in batch mode and continuously stirred (200 rpm). The immobilizates were separated from the fermentation medium after the saccharide substrate consumption and were used in a new fermentation. The series of 9 batch fermentations was performed in the similar way under the following conditions: the second up to fifth conversion occurred at the temperature of 50° C. and pH 6.0 and the sixth to tenth one at the temperature of 52° C. and pH value of 6.3. The total fermentation duration was shortened during the repetitive fermentations from 48 hours (the first conversion) to 12 hours (the tenth conversion) at the lactic acid yield of 91 to 93%. The biomass concentration in PVA gel increased to 0.065 $g_{cells}/g_{immobilizate}$ after the tenth conversion.

EXAMPLE 5

The media composition, the immobilizate preparation and the batch fermentation were analogical to those above mentioned in the Example 4, just glucose instead of saccharose was used in the production medium (60 g/l). There was 55.2 g/l of lactic acid and 1.2 g/l of glucose in the tenth conversion after 14 hours of fermentation.

EXAMPLE 6

350 g of the wet immobilizates prepared as described above in Example 4 was moved to 6 l fermentor and 2 dm³ of the production medium was added, which contained: 60 g of saccharose, 5.0 g of yeast extract, 0.8 g of $(NH_4)_2HPO_4$, 0.2 g of $MgSO_4 \times 7H_2O$, 0.05 g of $MnSO_4 \times 4H_2O$, 0.01 g of $FeSO_4 \times 7H_2O$ in 1 l of distilled water. Fermentation was performed in the batch way, permanently stirred (200 rev/min) at the temperature of 52° C., pH was kept on the value of 6.3 by addition of the ammoniac solution (26%). 2 l of the production medium of the same composition with the content of 140 g/l saccharose were then gradually batch after the saccharose concentration decrease to 20 g×dm$^{-3}$ at the rate, at which the concentration in fermentor could be kept in the range from 15 g/l to 30 g/l. The content of the lactic acid in medium was 93.5 g×dm$^{-3}$ after 15 hours, residual saccharose was 2.6 g/l.

EXAMPLE 7

The media composition and the preparation of the immobilizates were identical to those above mentioned in the Example 5. 350 g of the immobilizates was moved to the 6 l fermentor after 10. conversion and 2.5 dm³ of the production medium was added, which contained 60 g glucose, 5.0 g yeast extract, 0.8 g of $(NH_4)_2HPO_4$, 0.2 g of $MgSO_4 \times 7H_2O$, 0.05 g of $MnSO_4 \times 4H_2O$, 0.01 g of $FeSO_4 \times 7H_2O$ in 1 l of distilled water. Fermentation was permanently stirred (200 rpm) at the temperature of 52° C., pH was kept on the value of 6.3. The production medium was gradually batch after the glucose concentration decrease to 20 g×dm$^{-3}$ and fermented medium of the same composition was taken away in such way to keep the residual saccharose concentration in the reactor in the range of 15 g/l to 30 g/l, to keep the residual glucose concentration in the range of 10 g/dm³ to 15 g/dm³ and the actual lactic acid concentration in the range of 40 g·dm$^{-3}$ to 48 g·dm$^{-3}$. The fermentation was performed continuously for 40 days, average device volume productivity ranged from 13.5 to 17.0 ($g_{lactic\ acid} \times dm^{-3} \times h^{-1}$) in the process.

The method for the production and use of the above mentioned carriers in the process of the ethanol production from saccharide substrates by means of *Zymomonas mobilis* immobilized cells into polyvinyl alcohol gel will be illustrated by the following examples.

EXAMPLE 8

100 ml of the culture medium in 250 ml cultivation flask (sterilized for 20 min. at the temperature of 121° C.) was prepared. The culture medium contained 5 g of the yeast extract, 1 g of $(NH_4)_2SO_4$, 0.5 g of $MgSO_4 \times 7H_2O$, 1 g of $KH_2PO_4$, 100 g of glucose (pH from 5 to 5.5) in 1 l of distilled water. So the medium prepared was inoculate with the *Zymomonas mobilis* CCM 2770 culture, which had grown on the solid culture medium and was cultivated statically for 24 to 48 hour at the temperature of 30° C. The biomass thus prepared was used as inoculum (10% v.) into 100 ml of culture medium of the above described composition in 250 ml cultivation flasks. The microorganism was again moved into the culture medium (5% v.) after 12 hour static cultivation at the temperature of 30° C. Cultivation was performed at the temperature of 30° C. till the biomass dry matter value was 1.2 g×dm$^{-3}$, it is useful to stir the medium slightly. The biomass was separated by centrifugation (5500 rev/min., 25 min) after the cultivation finished and used in immobilization.

The PVA solution containing 100 g of PVA (polyvinyl alcohol), 60 g of PEG (polyethylene glycol) and 790 g of distilled water was prepared. 50 ml of the homogenous biomass suspension was added into thus prepared solution in such way, that the result cell concentration was 0.56 g of cells per 1 dm³ of gel. Thus prepared cell mixture in PVA solution was dropped onto a hard plate and then was cross-linked and shaped in a dry air stream in the temperature gradient of: 80° C. to 15° C. Immobilizates, ratio of the surface to the volume of which was minimally 7 mm$^{-1}$, were then moved into the sodium sulfate solution (0.1 mol/l) for 30 to 60 minutes.

The bacteria biomass in immobilizates was propagated in the 6 dm³ laboratory fermentor, each time with 3 dm³ of a sterile culture medium in the fermentation process, then: 23% v. of the immobilizate in culture medium was cultivated by the batch way while stirred constantly (80 rev/min), so that culture medium pH was adjusted to 6.5 and spontaneously decreased to pH=4.0 at the temperature of 25° C. Fluid phase was removed and a fresh medium was added to the immobilizates and the process was repeated once. Fluid phase was then removed and a fresh medium was added to the immobilizates and the pH value was adjusted to 6.5 (by 1M solution of NaOH). The pH value then decreased to pH=5 by spontaneous fermentation while permanently stirred (80 rpm), and then the fermentation was performed till a glucose depletion. Fluid phase was removed and a fresh medium was added to the immobilized cells and the process was repeated 6 times. A cell dry matter in thus prepared immobilizates increased to 65.8 g of cells/dm³ of gel.

2.2 dm³ of a sterile production medium with glucose content of 150 g×dm⁻³ and pH=5.5 was added to thus prepared immobilized cells (450 g of the wet biocatalyst). Fermentation occurred in the 5 l bioreactor permanently stirred (80 rpm), pH was kept at 5.0 by adding of the NaOH (2 mol/dm³) solution at the temperature of 30° C. This medium contained 73.8 g·dm⁻³ of ethanol after 11 hours of fermentation, while residual glucose concentration was 1.8 g·dm⁻³. The specific productivity of $Zymomonas\ mobilis$ ethanol immobilized into PVA carrier achieved 202 $mg_{ethanol}/ml_{gel}/h$.

EXAMPLE 9

450 g of the wet immobilizates, prepared as described above in Example 8, was added do 2.2 dm³ of the production medium with glucose content of 200 g·dm⁻³ (pH=5.0). Fermentation occurred in the batch way, permanently stirred (80 rpm), pH was kept at 5.0 by addition of the NaOH (2 mol·dm⁻³) solution at the temperature of 30° C. Six fermentations were performed in that way. The ethanol content in a medium was minimally 94.0 g·dm⁻³ to 98.0 g·dm⁻³, after each conversion, after 13 hours, and the residual glucose was 3 g·dm⁻³ to 8 g·dm⁻³ (i.e. 94% to 98% of theoretic yield).

EXAMPLE 10

The immobilizates prepared and propagated as described above in Example 9 were used. 1050 ml of a production medium with the glucose concentration of 150 g·dm⁻³ (immobilizates formed 30% of the fermentation medium volume) was added to 450 g of immobilizates. Fermentation occurred in the batch way, permanently stirred (80 rpm), pH was kept at 5.0 by addition of the NaOH (2 mol/dm³) solution at the temperature of 30° C.: 1500 ml of a culture medium with the glucose concentration 320 g·dm⁻³ was gradually batch, after the glucose concentration decreased to the value of 20 g·dm⁻³, at such rate to keep the residual glucose concentration in fermentor from 15 g·dm⁻³ to 30 g·dm⁻³. The ethanol content in a medium was 113.5 g·dm⁻³, i.e. 91% of theoretic yield, after 20 hours, the residual glucose was 4.6 g·dm⁻³.

EXAMPLE 11

The $Z.\ mobilis$ CCM 2770 immobilizates prepared and propagated as described above in Example 8 were used. 450 g of the wet immobilizates was moved into 2.2 dm³ of a culture medium with 150 g·dm⁻³ glucose, pH adjusted to 5.0. Fermentation occurred at pH=5.0 and at the temperature of 30° C. A culture medium with the glucose content of 50 g·dm⁻³ was continually batch, after the glucose content decreased in a fermentor to the value of 10 g·dm⁻³ to 20 g·dm⁻³, and fermented medium was removed in such dilution rate, that the residual glucose concentration in fermentor was in range of 17 g·dm⁻³ to 30 g·dm⁻³ and actual ethanol concentration in range of 58 g·dm⁻³ to 65 g·dm⁻³. Fermentation was performed continuously for 50 days, while the voluminal productivity of the device was 30 $g_{ethanolu}·dm^{-3}·h^{-1}$, which corresponds to the specific ethanol production of 140 $mg_{ethanol}/ml_{gel}/h$.

EXAMPLE 12

The procedure is the same as in example 8, $Zymomonas\ mobilis$ subsp. $pomacii$ CCM 2771 was used as a production microorganism. The medium contained 68.3 g·dm⁻³ of ethanol after 15 hour fermentation, while the residual glucose concentration was 6.8 g·dm⁻³.

The method for the production and use of the above mentioned carriers in the preparation of invert sugar from saccharose solutions by means of encapsulated invertase in polyvinyl alcohol gel will be illustrated by the following examples.

EXAMPLE 13

PVA solution was prepared, which contained 100 g of PVA (polyvinyl alcohol), 60 g of PEG (polyethylene glycol), 790 g of distilled water. 50 ml of enzyme preparation Invertase (Sigma) (enzyme concentration 100 g/l) was added into so the solution prepared. Thus prepared enzyme mixture in PVA solution was dropped onto a hard plate and then cross-liked and shaped in a dry air stream at the temperature gradient of: 80° C. to 15° C. the immobilizates, the ratio of the surface to the volume of which was minimally 7 mm⁻¹, were moved into the sodium sulfate solution (0.1 mol/l) for 10 to 120 minutes. The prepared immobilizates can be stored in the 10 mM of the acetate buffer solution (pH=4.5) at the temperature of 4° C.

Thus prepared immobilized enzyme can be used in the hydrolysis of saccharose solved in 10 mM of acetate buffer with pH=4.5. 120 g of immobilized invertase was added 1000 ml of saccharose solution (100 g/l). Hydrolysis was performed at permanent stirring (80 rpm) in the batch way at the temperature of 30° C. Saccharose is completely hydrolyzed after 50 minutes of hydrolysis into glucose and fructose.

EXAMPLE 14

120 g of the wet immobilizates, prepared as described above in Example 13, was added into 1000 ml of saccharose solution with the concentration of 450 g/l (pH=4.5, acetate buffer 10 mM) at the temperature of 30° C. Hydrolysis occurred in the batch way, continuously stirred. The residual saccharose concentration is 10.1 g/l in that way after 360 minutes.

EXAMPLE 15

120 g of wet immobilizates, prepared as described above in Example 13, was added into the 1000 ml of saccharose solution with the concentration of 280 g/l (pH=4.5, acetate buffer 10 mM) at the temperature of 30° C. Hydrolysis was performed in the batch way, permanently stirred. The residual saccharose concentration is in this way 1.8 g of/l after 360 minutes. The fluid phase was removed after hydrolysis, and immobilized invertase was used in repeated batch hydrolysis by the above mentioned procedure. The residual saccharose concentration after 240 minutes of hydrolysis was 3 g/l after 6 conversions.

EXAMPLE 16

The immobilizates prepared as described above in Example 13. 25 g of wet immobilizates was moved into 0.5 l of molasses with saccharose concentration of 120 g/l, pH 4.5 (adjusted by $H_2SO_4$). Hydrolysis was performed at pH=4.5, 30° C. and stirring 200 rpm. The molasses with the concentration of 120 g/l was continuously batched into the fermentor, and hydrolyzed medium was removed in such rate to achieve the saccharose concentration of 30 g/l to 40 g/l (66% to 75% conversion), after the saccharose amount in fermentor decreased into the value of 30 g/l to 40 g/l. The specific activity of the immobilizate is 0.35 g/g·h$^{-1}$ (g of the repute saccharose per g of the immobilizer per hour) in such mode.

EXAMPLE 17

The immobilizates prepared as described above in Example 13 were used. 25 g of wet immobilizates was moved into 0.5 l of molasses with saccharose concentration of 120 g/l, pH 4.5. Hydrolysis occurred at pH=4.5, temperature 45° C. and stirring 200 rpm. The molasses with the concentration of 120 g/l was continuously batched into the fermentor, and hydrolyzed medium was removed in such rate to achieve the saccharose concentration of 30 g/l to 40 g/l (66% to 75% conversion), after the saccharose amount in fermentor decreased into the value of 30 g/l to 40 g/l. The specific activity of the immobilizate is 0.55 g/g·h$^{-1}$ to 0.60 g/g·h$^{-1}$ (g of repute saccharose per g of immobilizer per hour) in such mode of hydrolysis, which is performed continuously for 500 hours.

The method for production and use of the above mentioned carriers in the glucose production process from the starch hydrolysates by means of encapsulated glucoamylase into polyvinyl alcohol gel will be illustrated by the following examples.

EXAMPLE 18

The solution of PVA was prepared, which contained 100 g of PVA (polyvinyl alcohol), 60 g of PEG (polyethylenglycol), 790 g of distilled water. 50 ml of the enzyme preparation SUN Ultra L (Novozymes) was added into thus prepared solution. Thus prepared mixture of enzyme in PVA solution was dropped onto a hard plate and then was cross-linked and shaped in a dry air stream at temperature gradient of: 80° C. to 15° C. The immobilizates, the ratio of the surface to the volume of which is minimally 7 mm$^{-1}$, were then moved into the sodium sulfate solution (0.1 mol/l) for 10 to 120 minutes. The prepared immobilizates can be stored in 30% w. glucose, dissolved in 10 mM of acetate buffer solution (pH=4.5) at the temperature of 4° C.

Thus prepared immobilized enzyme was used in hydrolysis of starch hydrolysate, for example, maltose molasses (composition: high saccharides 33% of weight, maltotriose 20% of weight, maltose 53% of weight, glucose 4% of weight), dissolved into 10 mM of acetate buffer solution with pH=4.5. 120 g of immobilized glucoamylase was added to 1000 ml of thus prepared solution with saccharide concentration of 100 g/l. Hydrolysis performed permanently stirred (200 rpm) in the batch way at the temperature of 30° C. The medium contained 70 g/l to 80 g/l of glucose after 60 minutes of hydrolysis.

EXAMPLE 19

5000 ml of maltose medium with concentration of 250 g of saccharides/l (pH=4.5) was added to 200 g of wet immobilizates, prepared as described above in Example 18 at the temperature of 40° C. Hydrolysis occurred in the batch way, permanently stirred. 180 g/l of glucose was created in this way in 6 hours. The fluid phase was removed after hydrolysis and the immobilized glucoamylase was used in repeated batch hydrolyses in the above mentioned procedure. The concentration of the produced glucose is 178 g/l after 6 hours of hydrolysis after the sixth conversion.

EXAMPLE 20

The immobilizates prepared as described above in Example 18 were used. 25 g of wet immobilizates was moved into 0.5 l of maltose molasses with the saccharide concentration of 100 g/l, pH 4.5. Hydrolysis occurred at pH=4.5, temperature of 30° C. and stirring 200 rpm. The maltose molasses with the saccharide concentration of 100 g/l was continuously batched into the fermentor and a hydrolyzed medium was removed in such rate to achieve the glucose concentration of 50 g/l to 60 g/l (50% to 60% conversion) after the glucose concentration increase in fermentor to the value of 55 g/l to 65 g/l. The specific activity of the immobilizer is 0.3 g/g·h$^{-1}$ to 0.4 g/g·h$^{-1}$ (g of the produced glucose per g of the immobilizate per hour), in that mode of hydrolysis performed continuously for 900 hours.

EXAMPLE 21

The immobilizates prepared as described above in Example 18 were used. 25 g of wet immobilizates was moved into 0.5 l of maltose molasses with the saccharide concentration of 100 g/l, pH4.5. Hydrolysis occurred at pH=4.5, temperature of 45° C. and stirring 200 rpm. The maltose molasses with the saccharide concentration of 100 g/l was continuously batched into the fermentor and a hydrolyzed medium was removed in such rate to achieve the glucose concentration of 60 g/l to 70 g/l (60% to 70% conversion) after the glucose concentration increase in fermentor to the value of 55 g/l to 65 g/l. The specific activity of the immobilizate was 0.55 g/g·h$^{-1}$ to 0.6 g/g·h$^{-1}$ (the produced glucose per g of the immobilizate per hour), in that mode of hydrolysis performed continuously for 1500 hours.

EXAMPLE 22

The immobilizates prepared as described above in Example 18 were used. The medium with the composition of: maltose molasses with the saccharide concentration of 195 g/l, yeast extract 5 g/l, $(NH_4)_2SO_4$, 1 g/l, $MgSO_4 \times 7H_2O$, 0.5 g/l, $KH_2PO_4$, 1 g/l, all dissolved in distilled water, pH=4.5. 50 g of the immobilizer with the immobilized glucoamylase was added to 1 l of thus prepared sterile medium. The suspension was then inoculated with 10% vol. *Zymomonas mobilis* inocula in the exponential growth period of microorganism. Simultaneous utilizing of the nascent glucose and the production of ethanol by means of microorganism occurred in the hydrolysis process. 70 g/l of ethanol was produced in this way in 13.5 hours.

EXAMPLE 23

The immobilizates prepared as described above in Example 18 were used. The medium with the composition of:

maltose molasses with the saccharide content of 80 g, 10 g of yeast extract, 1 g of $(NH_4)_2HPO_4$, 0.2 g of $MgSO_4 \times 7H_2O$, 0.05 g of $MnSO_4 \times 4H_2O$, 0.01 g of $FeSO_4 \times 7H_2O$ all dissolved in 1 l distilled water, pH=6.0 was used in conversions. 50 g of the immobilizate with immobilized glucoamylase was added into 1 l of thus prepared sterile medium. The suspension was inoculated with 5% vol. of *Bacillus coagulans* spore suspension. The simultaneous utilization of the nascent glucose and the lactic acid production by means of microorganism occurs in the hydrolysis process. There is 55.2 g/l of lactic acid and 1.2 g/l of glucose in a medium after 24 hours of fermentation.

The method for production and use of the above mentioned carriers in hydrolysis of lactose solutions, in D-galactose, D-glucose and galactooligosaccharides preparation by means of β-galactosidase encapsulated into polyvinyl alcohol gel, will be illustrated in the following examples.

EXAMPLE 24

The PVA solution was prepared, which contained 100 g of PVA (polyvinyl alcohol), 60 g of PEG (polyethylene glycol), 790 g of distilled water. 50 ml of the Lactozyme (Novozymes) enzyme preparation was added into thus prepared solution. Thus prepared mixture of the enzyme in the PVA solution was dropped onto a hard plate and then cross-linked and shaped in a dry air stream at temperature gradient of: of 80° C. to 15° C. The immobilizates, the ratio of the surface to the volume of which is minimally 7 $mm^{-1}$, were then moved into the solution of the phosphate buffer potassium, (pH=6.5) for 10 to 120 minutes. The prepared immobilizates can be stored in phosphate buffer solution (pH=6.5) with the addition of ethanol 5% to 10%, at the temperature of 4° C.

The immobilized enzyme prepared in that way had initial activity of 900±100 $U \cdot cm^{-3}$.

EXAMPLE 25

The immobilizates prepared as described above in Example 24 were used. The lactose solution in 0.1M phosphate buffer with pH=6.5 and with addition of 2 mM $MgCl_2$, was used in hydrolysis. 130 g of immobilized β-galactosidase was added into 1000 ml of thus prepared solution with the lactose concentration of 100 g/l. The hydrolysis occurred under permanent stirring (200 rpm), in the batch way, at the temperature of 30° C. The fluid phase was removed after hydrolysis and immobilized β-galactosidase was used in repeated batch hydrolyses in the above mentioned procedure. The medium contained 13 g/l to 2 g/l of lactose after 210 minutes of hydrolysis.

EXAMPLE 26

The immobilizates prepared as described above in Example 24 were used. The lactose solution in 0.1M phosphate buffer with pH=6.5 and with addition of 2 mM $MgCl_2$ was used in hydrolysis. 130 g of immobilized β-galactosidase with the initial activity of 786 $U \cdot cm^{-3}$ was added into 1000 ml of thus prepared solution with lactose concentration of 100 g/l. Hydrolysis occurred continuously stirred (200 rev/min.) in the batch way at the temperature of 30° C. The duration of conversion was constant. The immobilizer activity decrease by 5% to 10% was observed after 25 batch hydrolyses, which generally lasted 160 hours.

The arrangement of the casting device for the production of immobilizates, based on the polyvinyl alcohol carrier, which are mentioned in the above examples, will be explained in the further text. It is obvious, that the following description just illustrates the principles of an application of the invention principles.

The picture 1 shows the present construction version of the casting device for the production of the immobilizates based on a polyvinyl alcohol carrier, in adjustment for the continual industrial production. The construction version includes the dropping casting assembly, situated in front of the upper drying channel 2, which is formed by the dropping casting double-row head or heads 17, which is (are) equipped with two rows of the casting injectors and connected to the pressure tempered tank 15 and a compressor or a pressure air reservoir 16. The upper drying channel 2, inside which a continuous conveyor belt 1 with controlled drive runs, is equipped with a drying system—the source 4 of a drying air, from which the dehumidified air is transported through the first auxiliary ventilator 19 into the air distribution system 6 with integrated heating elements 5, which runs into the upper drying channel 2 at several points. The continuous conveyor belt 1, after leaving the upper drying channel, runs through the reswelling tank 7 and the final drying channel 3, which is situated on the opposite—bottom side of the casting device, into one side of which the pipeline leads with the second auxiliary ventilator 20 for the transport of a drying air from the upper drying channel, used for the conveyor belt final drying after leaving the rinse box 13, and from the other side of which the output 18 of a wet waste air leads out. The wipable collecting device 9, designed on the principle of mechanic wiping and high-pressure rinse, which is connected with the collecting reservoir 8, containing the solution of reswelling collecting salts 24 and equipped with cooling, by the pipeline with integrated high-pressure pump 10 and low-pressure pump 11, and the rinse box 13, for cleaning the continuous conveyor belt 1 by means of the jets joined to the low-pressure-pump 14, which is connected by the pipeline with the rinse lank 12 containing demineralized water, are integrated between the reswelling tank 7 with the reswelling salts solution 24 and the final drying channel 3.

The function of the device for the immobilizates production based on the polyvinyl alcohol carrier is as following: The mixture of the polyvinyl alcohol gel and the biological matter is transferred or poured, from the dropping casting assembly, formed by two casting heads 17 equipped with two rows of casting needles, the diameter of which is 0.1 to 2.00 mm, pulsating by means of electromagnets of different frequency and pulse length, onto continuous conveyor belt 1 with the controlled drive, which runs through the upper drying channel 2. The mixture for dropping, casting is batched into the pressure tempered tank 15, which is connected to the compressor or the pressure air tank 16. The mixture drying on the conveyor belt 1 is secured by a free of moisture-water air obtained from the continual atmospheric dehumidifier 4, which runs over the first auxiliary ventilator 19 and the heating elements 5, placed in the air conditioning distribution pipeline 6, which controls the temperature gradient in the upper drying channel and which leads into each segment of the upper drying channel 2. The dried mixture, adhered, stuck onto the continuous conveyor belt 1 then runs through the reswelling tank 7 with the reswelling salts solution, after which the products, i.e. immobilizates based on polyvinyl alcohol carrier, are detached in the collecting wipable device 9. This device is equipped with the system for the high-pressure water supply, formed by high-pressure pump 10 and jets, and that system is connected to the independent circuit. The products detaching from the conveyor belt occurs by means of the polymer wipable blade and the jets by an aqueous salt solution supplied by high-pressure pump 10. The conveyor belt 1 is finally treated by means of the jets situated in the rinse box 13, low-pressure pump 14 and the rinse demineralized water is collected in the rinse tank 12, into which it flows down from the rinse box 13. The low-pressure water delivery system for the conveyor belt rinse is connected to the independent circuit. The wet conveyor belt 1 is then finally dried in the lower drying channel 3, into which a drying air is blown from the upper drying channel through the pipeline, in which the second auxiliary ventilator 20 is installed, while the wet waste air is conducted away from lower drying channel 3 through the wet waste air outfall 18.

The picture 2 shows the construction of the reswelling tank. The reswelling tank 7 in this version consist of the tank 21 with an oblique bottom, in the lowest point of which the outlet valve 22 is situated for letting out the product and the reswelling salts solution. The conveyor belt 1, led by the couple of leading tension rollers 23, which simultaneously specify the conveyor belt immersion into the reswelling aqueous salt solution 24, by which the tank 21 is filled up, runs through the tank 21.

The picture 3 shows the construction of the wipable collecting device 9. The wipable collecting device 9 in this version consists of side frame 25, in which the mechanic polymer wiper is situated on the stainless pressure assembly 27 with the spring pressure assembly 28. That spring pressure assembly 28 is formed by thrust regulation screw 34 with washer, on which the spring 35 is placed. The wipable collecting device 9 is further formed by high-pressure jets 26, joined on the supporting stainless pipe distribution system fixed in the frame 25, which enable the rinse at the angle of 45° to 80°. The stainless pipe distribution system 30, is equipped with the altitudinal regulation, which is secured by the regulation screws 31. The lower and the upper wiper 29, with the polymer brushes 32 which are fixed on the upper frame 33, while the conveyor belt 1 runs between those wipers, are firmly situated on its inner and also outer side behind the mechanic wiper 27, for the cleaning of the inner side of the conveyor belt. The conveyor belt is equipped with lower and also the upper polymer wiper 29 for the final treatment of the inner and also the outer side of the conveyor belt 1 at the point of its way our of the frame 25.

The wiping collecting device 9 function is tooled to the production line behind the reswelling tank 7, from which the conveyor belt 1 runs out already from the lower section of the device, hence in opposite direction. It is obvious, that the product applied in the upper device section onto the conveyor belt 1 is now upside down in vertical position. The method for its removal from the conveyor belt is based on the fact that the mechanical wiper 27 and also the high-pressure jets 26 affect in cooperation the product adhered on the outer side of the conveyor belt 1. The product on the conveyor belt 1 is at first led to the high-pressure rinse, which is ensured by the pressure distribution system of the aqueous salt solution delivered by pressure jets 26, which work at the angle of 40° to 80° against the mechanical wiper 27 with the spring pressure mechanism 28, an inclination towards the conveyor belt 1 of which is also controllable in range of 5° to 15°. The lower and the upper firmly fixed wipers 29, with the polymer brushes, which simultaneously final treat the conveyor belt 1 on its inner and also outer side, are mounted behind the sprung mechanical polymer wiper 27 on the stainless pressure assembly 28. The conveyor belt 1 leaves the frame 25 over the lower and the upper polymer wipers 29, by which it is final treated on both sides.

The picture 4 shows the construction of the rinse box 13. The rinse box 13 in this version is formed by the upper part 36 with the lid 43 and the lower part 37 with the outlet 38 connected to each other, between which the conveyor belt 1 runs while these parts are connected to the casting machine frame 39. Furthermore, the upper rinse jet 40 connected to the rinse water supply pipe 41 is mounted in the upper part 36 and in the same way the lower rinse jet 42 connected to the supply pipe 41 is mounted in the lower section 37. The adjustable polymer wipers 44 are fixed on both sides of the upper section 36 for wiping of water from the conveyor belt and in the same way wipers 45 are fixed on both sides of the lower part 37. The rinse box 13 is fixed to the casting machine frame 39 by the upper and the lower assembling segments 46 and 47.

INDUSTRIAL UTILITY

The present invention can be used in the production of the immobilizates, which are intend for applications in food industry, pharmacy and in waste water treatment, in particular in nitrogen compounds biological removing from drinking, supply and waste waters (waste, agricultural, municipal, industrial waste waters), present in which various nitrogen compounds are converted into gaseous nitrogen by physiological activity of nitrifying and denitrifying bacteria, and further in the production process of lactic acid, ethanol, glucose and glucose-fructose molasses, in lactose hydrolysis into D-galactose and in galactooligosaccharides production. All of them are produced by means of the device which provides continuous industrial production with the capacity of 1 kg to 10 kg of the immobilizates of LentiKats™ per hour.

The device for the production of the immobilizates, destined for the food industry, pharmacy applications and for waste water treatment, can be used in continuous production.

THE LIST OF RELATED SYMBOLS

1—conveyor belt with controlled drive
2—upper drying channel
3—lower drying channel
4—drying air source—continuous adsorption dehumidifier
5—heating elements on air pipeline
6—drying air distribution system
7—reswelling tank in the lower section of the production casting device
8—collecting reservoir with cooling
9—collecting high-pressure devise
10—high pressure pump
11—delivery low-pressure pump
12—rinse tank
13—rinse BOX
14—rinse low-pressure pump
15—pressure tempered 10 l to 12 l tank
16—compressor
17—casting dropping head
18—outfall of a waste wet air
19—the first ventilator
20—the second ventilator
21—tank
22—escape cock
23—tension roller
24—reswelling salt solution
25—side frame
26—jets
27—mechanical wiper
28—pressure spring mechanism
29—upper, lower wiper
30—distributing pipe
31—adjusting screws
32—brush

33—upper protective frame
34—thrust regulation screw
35—spring
36—upper section of the box
37—lower section of the box
38—outfall
39—casting machine frame
40—upper rinse jet
41—supply pipe
42—lower rinse jet
43—lid
44—adjustable wiper
45—wiper
46—upper assembling segment
47—lower assembling segment

The invention claimed is:

1. An industrial production device for producing an immobilized biocatalyst comprising:

a continuous conveyor belt;

a casting mechanism mounted above the conveyor belt for applying a mixture containing a biocatalyst to the conveyor belt, the casting mechanism positioned in front of an upper drying channel through which the conveyor belt passes, the casting mechanism comprising at least one casting head with two rows of casting needle injectors through which the mixture is fed to the conveyor belt by a pressure regulated tank and a compressor, the upper drying channel disposed to deliver drying air to the mixture on the conveyor belt to dry the mixture and immobilize the biocatalyst, the drying air being blown by means of a ventilator into an air distribution system with incorporated heating elements to the upper drying channel;

a reswelling tank, after the upper drying channel, through which the conveyor belt containing immobilized biocatalyst passes;

a wiping and collecting device after the reswelling tank, through which the conveyor belt passes to remove and collect immobilized biocatalyst from the conveyor belt, the wiping and collecting device comprising a mechanical wiper and a high-pressure rinser, the high-pressure rinser connected to a respective pipeline with an integrated high-pressure pump and a low-pressure pump, and the mechanical wiper connected to a collecting reservoir capable of cooling where the immobilized biocatalyst is collected;

a rinse box, after the wiping and collecting device, through which the conveyor belt passes to clean the conveyor belt after removing the immobilized biocatalyst, the rinse box comprising jets connected to a low-pressure pump, which is connected to a rinse tank by means of a respective pipeline; and a lower drying channel, after the rise box, through which the conveyor belt passes to dry the conveyor belt.

2. The industrial production device of claim 1, wherein the wiping and collecting device comprises a frame through which the conveyor belt containing immobilized biocatalyst passes, the mechanical wiper is fixed to the frame by means of a spring pressure mechanism, and the high pressure rinser comprises high pressure jets fixed to the frame to enable rinsing at an angle of 45° to 80°, the mechanical wiper and high pressure rinser are fixed to the frame at positions such that the conveyor belt containing immobilized biocatalyst passes the high pressure rinser and then the mechanical wiper such that the mechanical wiper and high pressure rinser function in cooperation to remove immobilized biocatalyst from the conveyor belt, and following the mechanical wiper, the frame further comprises fixed lower and upper wipers with brushes which the conveyor belt passes between for final cleaning of inner and outer sides of the conveyor belt as the conveyor belt leaves the frame.

* * * * *